US010780002B2

(12) United States Patent
Swedberg et al.

(10) Patent No.: US 10,780,002 B2
(45) Date of Patent: Sep. 22, 2020

(54) PANT-LIKE ABSORBENT ARTICLE

(71) Applicant: SCA Hygiene Products AB, Gothenburg (SE)

(72) Inventors: Maria Swedberg, Gothenburg (SE); Anders Silfverstrand, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 280 days.

(21) Appl. No.: 15/757,512

(22) PCT Filed: Sep. 18, 2015

(86) PCT No.: PCT/SE2015/050976
§ 371 (c)(1),
(2) Date: Mar. 5, 2018

(87) PCT Pub. No.: WO2017/048167
PCT Pub. Date: Mar. 23, 2017

(65) Prior Publication Data
US 2018/0243147 A1     Aug. 30, 2018

(51) Int. Cl.
*A61F 13/15* (2006.01)
*A61F 13/62* (2006.01)
(Continued)

(52) U.S. Cl.
CPC .......... *A61F 13/625* (2013.01); *A61F 13/496* (2013.01); *A61F 13/5638* (2013.01);
(Continued)

(58) Field of Classification Search
CPC ...... A61F 13/62; A61F 13/496; A61F 13/625; A61F 13/5638; A61F 13/5655; A61F 13/627; A44B 18/00
(Continued)

(56) References Cited

U.S. PATENT DOCUMENTS

| 4,672,722 A | 6/1987 | Malamed |
| 4,936,840 A * | 6/1990 | Proxmire .......... A61F 13/49011 |
| | | 604/385.22 |

(Continued)

FOREIGN PATENT DOCUMENTS

| CN | 1141234 A | 1/1997 |
| CN | 1303242 A | 7/2001 |

(Continued)

OTHER PUBLICATIONS

U.S. Appl. No. 60/112,775, filed Dec. 18, 1998, Olson.
(Continued)

*Primary Examiner* — Jacqueline F Stephens
(74) *Attorney, Agent, or Firm* — Buchanan Ingersoll & Rooney PC

(57) ABSTRACT

A pant-type absorbent article has a longitudinal direction, a transverse direction, an inner surface facing the user during use, an outer surface facing away from the user during use. The article includes: a first body portion, a second body portion and an intermediate crotch portion provided with two leg openings. Outer longitudinal edge portions of the first body portion are adapted to be interconnected to outer longitudinal edge portions of the second body portion by first and second longitudinal refastenable side seam configurations. Each one of the refastenable side seam configurations includes a fastening component bonded to an outer longitudinal edge portion of the first body portion and a mating fastening component bonded to a corresponding outer longitudinal edge portion of the second body portion. Moreover, each one of the fastening components and the mating fastening components includes a first mechanical connector structure and a second mechanical connector structure.

19 Claims, 9 Drawing Sheets

(51) Int. Cl.
*A61F 13/496* (2006.01)
*A61F 13/56* (2006.01)

(52) U.S. Cl.
CPC .......... *A61F 13/5655* (2013.01); *A61F 13/62* (2013.01); *A61F 13/627* (2013.01)

(58) Field of Classification Search
USPC ........ 604/386, 387, 389, 390, 391, 394, 396
See application file for complete search history.

(56) References Cited

U.S. PATENT DOCUMENTS

| | | | |
|---|---|---|---|
| 5,669,120 | A | 9/1997 | Wessels et al. |
| 6,575,953 | B2 | 6/2003 | Olson |
| 6,761,711 | B1 | 7/2004 | Fletcher et al. |
| 6,770,065 | B1 | 8/2004 | Sasaki et al. |
| 7,819,851 | B2 | 10/2010 | Karlsson |
| 8,052,666 | B2 | 11/2011 | Sawyer et al. |
| 2002/0138064 | A1 | 9/2002 | Datta et al. |
| 2003/0009144 | A1* | 1/2003 | Tanzer ................ A61F 13/5622 604/391 |
| 2003/0060794 | A1 | 3/2003 | Olson |
| 2003/0135190 | A1 | 7/2003 | Widlunc et al. |
| 2004/0006854 | A1 | 1/2004 | Simon |
| 2006/0293635 | A1 | 12/2006 | Petersen |
| 2007/0098953 | A1 | 5/2007 | Stabelfeldt et al. |
| 2014/0101901 | A1 | 4/2014 | Tuma |
| 2014/0115837 | A1 | 5/2014 | Dobrin et al. |

FOREIGN PATENT DOCUMENTS

| | | |
|---|---|---|
| CN | 1348348 A | 5/2002 |
| CN | 1925822 A | 3/2007 |
| CN | 101094638 A | 12/2007 |
| CO | 04-73403 | 7/2004 |
| DE | 196 51 835 A1 | 6/1998 |
| EP | 0741979 A2 | 11/1996 |
| EP | 1 559 386 A2 | 8/2005 |
| ES | 2460366 T3 | 5/2014 |
| GB | 972 648 A | 10/1964 |
| GB | 2299743 A | 10/1996 |
| JP | S57118718 U | 7/1982 |
| JP | H0716109 A | 1/1995 |
| JP | H08299032 A | 11/1996 |
| JP | 2002532195 A | 10/2002 |
| WO | 95/27462 A1 | 10/1995 |
| WO | 00/35396 A1 | 6/2000 |
| WO | 0037009 A2 | 6/2000 |
| WO | 02/069864 A2 | 9/2002 |
| WO | 03057121 A1 | 7/2003 |
| WO | 2007/050253 A1 | 5/2007 |
| WO | 2012052884 A2 | 4/2012 |
| WO | 2013072787 A1 | 5/2013 |

OTHER PUBLICATIONS

International Search Report (PCT/ISA/210) dated Jun. 1, 2016, by the Swedish Patent Office as the International Searching Authority for International Application No. PCT/SE2015/050976.
Written Opinion (PCT/ISA/237) dated Jun. 1, 2016, by the Swedish Patent Office as the International Searching Authority for International Application No. PCT/SE2015/050976.
International Report on Patentability (PCT/IPEA/409) dated Sep. 8, 2017, by the Swedish Patent Office as the International Searching Authority for International Application No. PCT/SE2015/050976.
Office Action (Notice of Reasons for Rejection) dated Apr. 1, 2019, by the Japanese Patent Office in corresponding Japanese Patent Application No. 2018-514343, and an English Translation of the Office Action. (13 pages).
The extended European Search Report dated Apr. 11, 2019, by the European Patent Office in corresponding European Application No. 15904214.2. (4 pages).
English Translation of the Search Report and Written Opinion dated Mar. 14, 2020, by the Brazilian Patent Office in corresponding Brazilian Application No. BR112018002075-3. (4 pages).
Office Action issued in corresponding Mexican Patent Application No. MX/a/2018/003262, dated Oct. 7, 2019, with partial translation.
Office Action dated Jun. 7, 2019, by the Colombian Patent Office in corresponding Colombian Patent Application No. 2018/0002825, and an English Translation of the Office Action. (16 pages).
Office Action (Notice of Allowance) dated Aug. 29, 2018, by the Australian Patent Office in corresponding Australian Patent Application No. 2015409412. (3 pages).
Office Action (Decision to Grant) dated Aug. 20, 2018, by the Russian Patent Office in corresponding Russian Patent Application No 2018114066, and an English Translation of the Office Action. (17 pages).
Office Action (Decision of Rejection) dated Nov. 25, 2019, by the Japanese Patent Office in corresponding Japanese Patent Application No. 2018-514343, and an English Translation of the Office Action. (9 pages).
Notification of the Third Office Action dated Apr. 3, 2020, by the Chinese Patent Office in corresponding Chinese Patent Application No. 201580083171.8, and an English Translation of the Office Action. (20 pages).

\* cited by examiner

PANT-LIKE ABSORBENT ARTICLE

TECHNICAL FIELD

This disclosure relates to a disposable pant-type absorbent article, such as a pant diaper, a sanitary pant or incontinence pant. The article comprises, as seen in a longitudinal direction, a first body portion, a second body portion and an intermediate crotch portion provided with two leg openings, the crotch portion extending between the first body portion and the second body portion in the longitudinal direction of the article, wherein the outer longitudinal edge portions of the first body portion are interconnected to the outer longitudinal edge portions of the second body portion by first and second longitudinal refastenable side seam configurations.

BACKGROUND

Pant-type absorbent articles have a defined waist opening and a pair of leg openings and are pulled onto the body of the wearer by inserting the legs into the leg openings and pulling the article up over the waist. They are usually provided with various elastic elements so that they can conform to the body of the user and provide a comfortable fit. Examples of such pant-type absorbent articles are pant diapers, sanitary pants and incontinence pants worn by incontinent adults. They comprise a first body panel and a second body panel, forming the front and back panels of the pant. The first and second body panels are joined to each other along lateral edges to form side connections. A crotch panel is provided between the first and second body panels. The crotch panel can be integral with either one or both panels or can be provided as a separate part joined to the first and second body panels.

Over time, disposable absorbent articles, in particular pant-type absorbent articles, have continuously been further developed and some of them are now commonly provided with a refastening mechanism such as refastenable side seams that allows the garment to be easily removed after use or to be adjusted during use. However there are known through various prior art documents such refastenable pant-type absorbent articles. As an example, WO 95/27462 discloses a pant diaper having releasable and refastenable fastening means along the lateral edges of the front and back panels for joining the front and back panels together along the sides thereof. The refastenable fastening means replaces a permanent side seam.

SUMMARY

An object of the present disclosure is to provide a pant-type absorbent article such as a pant diaper, a training pant, a swim pant, a sanitary pant or incontinence pant, and to further improve the functionality of a refastenable side seam configuration of such article. This object is at least partly achieved by the features of claim 1.

The disclosure concerns a pant-type absorbent article such as a pant diaper, training pant, swim pant, sanitary pant or incontinence pant. The article has a longitudinal direction, a transverse direction, an inner surface facing the user during use, an outer surface facing away from the user during use. The article comprises, as seen in the longitudinal direction: a first body portion, a second body portion and an intermediate crotch portion provided with two leg openings, the crotch portion extending between the first body portion and the second body portion in the longitudinal direction of the article. Further, the outer longitudinal edge portions of the first body portion are interconnected to the outer longitudinal edge portions of the second body portion by first and second longitudinal refastenable side seam configurations.

Each one of the refastenable side seam configurations comprises a fastening component bonded to an outer longitudinal edge portion of the first body portion and a mating fastening component bonded to a corresponding outer longitudinal edge portion of the second body portion. Moreover, each one of the fastening components and the mating fastening components comprises a first mechanical connector structure and a second mechanical connector structure, each mechanical connector structure being capable of forming a mechanical interconnection with said other mechanical connector structure, and being incapable of forming a mechanical interconnection with an identical structure, whereby corresponding fastening component and mating fastening component of one refastenable side seam configuration are mechanically connectable via said first mechanical connector structure and said second mechanical connector structure to form an interconnection.

To this end, corresponding fastening component and mating fastening component of one refastenable side seam configuration are mechanically connectable via said first mechanical connector structure and said second mechanical connector structure to form an interconnection so as to form a pant-type configuration.

In this manner, there is provided a more secure connection between the fastening component and the mating fastening component of the refastenable side seam configuration. In addition, by the provision that each one of the fastening components and mating fastening components comprising first mechanical connector structure and second mechanical connector structure, as described above, it becomes possible to provide a high level of contact between the components. Furthermore, the mechanical interconnection provided by having two types of mechanical connector structures on each fastening component and mating fastening component contributes to minimize the risks of having a poor fastening of the pant-type absorbent article around the wearer during use. As a poor fastening often results in a poor fit of the article and an increased risk of leakage, the example embodiments of the disclosure may also have a positive impact on overall fit of the article, whilst reducing the risk of leakage during use of the article.

Due to that each one of the fastening components and the mating fastening components comprising both first mechanical connector structure and second mechanical connector structure, the peel strength and shear strength of the refastenable side seam configuration, when sealed, is further improved as the number and type of connection areas of the seam is increased in view of known side seam configuration having a fastening component comprising a hook material and a mating fastening component comprising a loop material.

In addition, the example embodiments of the disclosure provides the advantage that less considerations is needed as to the type of material of the body portions of the article because the interconnection to form the refastenable side seam configuration is made between the first mechanical connector structure and the second mechanical connector structure of the components, and thus not between e.g. a hook material on one body portion and another surface of the other body portion. The latter often requires that the material of the body portion acting as the receiving surface for the hook material is carefully selected in terms of fastening properties etc. Thus, the configuration of the fastening component and the mating fastening components may increase the design freedom of the material of the body portions, which is particularly applicable to articles made up of elastic side panels, e.g. articles in which the outer longitudinal edge portions includes an elastic region.

For the same reasons, the configuration of the fastening component and the mating fastening component results in that the materials making up the mechanical interconnection can be selected almost independent on type of material of the body portions, thus more optimal materials of the fastening component and the mating fastening component may be selected, which e.g. will reduce the amount of fuzz on the mechanical connector structure during use of the article, e.g. if the connector structure is a hook material, compared to an article having a hook material on one body portion to engage directly with a nonwoven material on the other body portion.

In addition to that, the configuration of the fastening component and the mating fastening component also allows using stiffer materials for the mechanical connector structures without compromising the function and quality of the materials of the body portion. Thus better fastening characteristics can be provided compared to e.g. a fastening configuration between a hook material engaging directly on an elastic body portion material. At least for these reasons, there is further no need for any additional external fastening member extending externally around the refastenable side seam configuration of the article, as in some prior art solutions.

The example embodiments of the disclosure further provides a pant-type absorbent article which is less prone to be reclosed in a misaligned or misplaced configuration.

Accordingly, there is provided an article having a refastenable side seam configuration which is more pliable, more flexible and less stiff than current prior art articles, whilst maintaining a high level of wearer comfort.

Further advantages are achieved by implementing one or several of the features of the dependent claims.

In the example embodiments, a fastening component thus typically comprises a first mechanical connector structure and a second mechanical connector structure, the first and second mechanical connector structures being two corresponding structures, each structure being capable of forming a mechanical interconnection with the other structure, and being incapable of forming a mechanical interconnection with an identical structure, whereby the fastening component is mechanically connectable to a mating fastening component, the mating fastening component comprising the first and second mechanical connector structures.

The terms "fastening component" and "mating fastening component" as used herein is generally a portion of material comprising first and second mechanical connector structures and which potentially (if in contact with another fastening component or mating fastening component) may perform interconnection of the body portion to another body portion by means of said first and second mechanical connector structures.

The mechanical connector structures herein refer to connector structures for mechanically interconnecting an outer longitudinal edge surface portion of one body portion of the article to another outer longitudinal edge surface portion of another body portion, as is typically required to form a pant-type configuration when the article is to be used.

Mechanical connector structures have the advantage of providing a secure connection between themselves, whilst not being prone to unwanted connection to other materials, such as to the body portion material itself. Hence, use of mechanical connector structures provides an improved and reliable connection of the refastenable side seam during use of the article, which is hitherto not provided by prior art articles.

Mechanical connector structures may often be of a type where the connection is accomplished by a pair of two different, corresponding interconnectable connector structures. The first connector structure is hence capable of forming a mechanical interconnection with a second connector structure, but not with another first connector structure (i.e. an identical structure). Similarly, the second connector structure is capable of forming a mechanical interconnection with the first connector structure, but not with another second connector structure (i.e. an identical structure). A typical example of such connector structures is a hook structure and a corresponding loop structure.

Typically, although not strictly required, the first and second connector structures are arranged in a pattern. It will be understood that the first and second mechanical connector structures are arranged on a first side of the fastening component. One of the first and second connector structures may comprise hooks, and the other of the first and the second connector structures may comprise loops.

Alternatively, one of said first and second connector structures may comprise a first type of hooks, and the other of the first and the second connector structures may comprises a second type of hooks, said first type of hooks having a different hook characteristics than said second type of hooks.

The first connector structure may be provided by a first connector material and the second connector structure may be provided by a second connector material.

According to example embodiments, the second connector material may be attached to the first connector material, preferably onto the first connector material.

According to example embodiments, the fastening component and the mating fastening component comprises a first connector material onto which intermittent pieces of second connector material are attached. The fastening component and the mating fastening component may comprise a first connector material onto which is attached a second connector material in which through holes are formed, such that the first connector structures of the first connector material is accessible via the through holes in the second connector material.

The fastening component and the mating fastening component may comprise a carrier material, onto which the first and/or second connector material is attached.

The fastening component and the mating fastening component may be a single connector material comprising a backing from which the connector structures extend.

The fastening component and the mating fastening component may display a repeated pattern for forming individual connectors.

The fastening component and the mating fastening component may each display a repeated pattern having a length and a width, preferably the length being a length with which the pattern repetition is evenly divisible.

It is proposed herein that each one of the fastening component and the mating fastening component of a refastenable side seam configuration, is to comprise first and second mechanical connector structures.

In accordance with the above, a pant-type absorbent article is provided which enables an improved refastenable side seam configuration, since each one of the fastening component and the mating fastening component of a refastenable side seam configuration comprising both first and second connector structures.

This is in contrast to a conventional refastenable side seam, in which e.g. a fastening component comprises a first connector structure only, and a mating fastening component comprises the second connector structure only, in which case an outer longitudinal edge region must be positioned with a first mechanical connector towards a second mechanical connector of another outer longitudinal edge region (or vice versa) to achieve mechanical interconnection. In such a case, the person performing the fastening operation must generally be more careful in order to achieve a correct and reliable interconnection.

To provide an interconnection, it is generally not required that the entire surface area formed by the first mechanical connector structure and/or the second mechanical connector structure of a fastening component is interconnected to a second and/or first mechanical connector structure of a mating fastening component. With mechanical fastening components, sufficient connection strength may be achieved already with relatively small interconnected areas of mechanical connector structures. Hence, to provide an interconnection, it may be sufficient that the fastening components are designed so as to enable interconnection between a portion of the first connector structure of the fastening component and a portion of a corresponding second structure of the mating fastening component, or vice versa.

Typically, said first mechanical connector structure and said second mechanical connector structure of said fastening component is arranged in a first pattern and the first mechanical connector structure and the second mechanical connector structure of said mating fastening component is arranged in a second pattern. Said first pattern and said second pattern are formed so that at least a portion of the first mechanical connector structure of said fastening component mirrors at least a portion of the second mechanical connector structure of said mating fastening component and at least a portion of the second mechanical connector structure of said fastening component mirrors at least a portion of the first mechanical connector structure of said mating fastening component.

The term "pattern" here refers to an organised arrangement of at least one area comprising the first mechanical connector structure, and at least one area comprising the second mechanical connector structure, in contrast to the random arrangement as described in the above. Further, the term "mirror", "mirroring" or "a mirror image" refers to the relative arrangement of the two mechanical connector structures in the first pattern and the two mechanical connector structures in the second pattern when said fastening component and said mating fastening component are joined so as to form the closed pant-type configuration. That is, the above provision refers to a mirroring of the portions when the article is formed into the pant-type configuration.

According to one example embodiment, said first mechanical connector structure and said second mechanical connector structure of said fastening component is arranged in a first pattern and the first mechanical connector structure and the second mechanical connector structure of said mating fastening component is arranged in a second pattern, said first pattern being a mirror image of said second pattern. As mentioned above, the term "mirror image" refers to the relative arrangement of the two mechanical connector structures in the first pattern and the two mechanical connector structures in the second pattern when said fastening component and said mating fastening component are joined so as to form the closed pant-type configuration.

Typically, the entire first pattern is a mirror image of the entire second pattern. In other words, the arrangement of the first mechanical connector structure and the second mechanical connector structure of said fastening component is a mirror image of the arrangement of the first mechanical connector structure and the second mechanical connector structure of said mating fastening component.

In this manner, the first mechanical connector structure and the second mechanical connector structure of the fastening component and the first mechanical connector structure and the second mechanical connector structure of the mating fastening component are capable of interconnecting over the entire area of the two different connector structures, thereby increasing the interconnection between the body portions to a maximum.

Typically, although not strictly necessary, the extension and orientation of the fastening component on one outer longitudinal edge portion, as seen in the direction x and direction y, corresponds to the extension and orientation of the corresponding mating fastening component on the other mating outer longitudinal edge portion, as seen in the direction x and the direction y.

In certain variants, the fastening component and the mating fastening component may be different in terms of shape, extension and pattern. In certain variants, the fastening component and the mating fastening component may be similar in terms of shape, extension and pattern.

The first and the second mechanical connector structures may be randomly arranged on the fastening component and the mating fastening component. In this case, the first and second mechanical connector structures may be provided by a connector material on which first and second connector structures are formed in a random arrangement. For example, such a connector material could be a compound material designed to interconnect with an identical compound material, comprising randomly arranged first and second mechanical connector structures, e.g. randomly arranged hooks and loops protruding from a common backing material. Alternatively, the first and second mechanical connector structures per se may be arranged in an organised manner on a common backing material, but on a scale which will still result in a random arrangement as seen over the at least one connector.

Alternatively, at least one of the first and second connector structures may be arranged to form a pattern over the corresponding surface of the fastening component.

With "a pattern" is meant herein an organised arrangement of at least one area comprising the first mechanical connector structure, and at least one area comprising the second mechanical connector structure, in contrast to the random arrangement as described in the above.

Such a pattern may be formed by various types of connector materials as will be described in the below. The pattern may be selected in various manners to provide sufficient likelihood of interconnection between the fastening component and the mating fastening component of one refastenable side seam configuration.

Optional, such a pattern of a fastening component may be adapted such that the pattern surface is mechanically connectable to an identical pattern surface, (i.e. provided with an identical pattern) of a mating fastening component.

In this disclosure, the term "identical" is meant herein something which is sufficiently identical considering the intended purpose of the features. Manufacturing tolerances or slight variations which do not affect the function of the feature is to be comprised in the term "identical".

Alternatively, such a pattern of a fastening component may be adapted such that the pattern surface is mechanically connectable to a different pattern surface, (e.g. provided with a different pattern) of a mating fastening component.

That mating outer longitudinal edge portions are mechanically connectable means that they may be connected, at least if a fastening component is provided with a specific orientation relative to the mating fastening component.

The fastening component may define a longitudinal central axis X, extending in parallel to the length of the component, and centrally in relation to the width of the component, wherein the pattern formed by the first and the second connector structures may be asymmetrical with respect to the longitudinal central axis X.

Patterns which are asymmetrical with respect to the longitudinal central axis, may be designed so as to provide interconnections independently of the relative orientation of the end surfaces.

The fastening component may define a transversal central axis Y, extending in parallel to the width of the component, and centrally in relation to the length of the component, wherein the pattern formed by the first and the second connector structures is asymmetrical with respect to the transversal central axis Y.

Patterns which are asymmetrical with respect to the transversal central axis, may be designed so as provide interconnections independently of the relative orientation of the fastening component and the mating fastening component.

The pattern formed by the first and the second connector structures may be such that at least a portion of the first structure on one side of the longitudinal central axis X, mirrors a portion of the second structure on the other side of the longitudinal central axis X, preferably all portions of the first structure on one side of the longitudinal central axis mirrors a portion of the second structure on the other side of the longitudinal central axis.

With (mating) fastening components comprising mirroring first and second structures over the longitudinal central axis may, interconnectivity between two similar fastening components and mating fastening components, regardless of their relative orientation may be achieved.

However, it is to be noted that the fastening component and the mating fastening component may necessarily not be identical in terms of shape and geometry, but that the width, length, pattern and/or shape of the fastening component may be different to the width, length, pattern and/or shape of the mating fastening component.

The pattern formed by the first and the second connector structures may be such that at least a portion of the first structure on one side of the transverse central axis Y, mirrors a portion of the second structure on the other side of the transverse central axis Y, preferably all portions of the first structure on one side of the transversal central axis Y mirrors a portion of the second structure on the other side of the transversal central axis Y.

With fastening components and mating fastening components comprising mirroring first and second structures as seen over the transversal central axis, a similar fastening component and a similar mating fastening component may be interconnected regardless of their orientation in relation to their transverse central axis.

In particular, at least one portion of the first structure, located on one side of the longitudinal central axis X and on one side of the transversal central axis Y; may mirror a portion of the second structure on the other side of the longitudinal central axis X and a portion of the second structure on the other side of the transversal central axis Y.

A fastening component (or mating fastening component) where at least one portion of the first structure mirrors a portion of the second structure over the longitudinal central axis X, and a portion of the second structure over the transversal axis Y, when mechanically interconnected, may be connected to another mating fastening component, regardless of the relative orientation of the components as long as they meet upon fastening of the article.

It may be that only one out of the first and the second connector structures is located on one side of the longitudinal central axis (X). This will be sufficient e.g. for forming e.g. a mirroring pattern as described in the above.

One of the first and the second connector structures may comprise hooks, and the other of the first and the second connector structures may comprise loops. Hook and loop materials providing sufficient strength and suppleness for the application intended herein are commercially available, e.g. under the trademark Velcro®.

Examples of suitable loop materials are knitted loop, brushed loop or a nonwoven loop materials. This type of materials are commercially available e.g. from 3M. Examples of suitable hook types are moulded hooks and textile hooks. The hooks can have different configurations, e.g. mushroom. Hook materials are commercially available e.g. from Velcro.

The fastening components and mating fastening components may each have a height of less than 2 mm, preferably less than 1 mm, most preferred less than 0.6 mm.

The first mechanical connector structure may be provided by a first connector material, and the second mechanical connector structure may be provided by a second connector material. For example, the first connector structure may be a loop material, and the second connector structure may be a hook material.

The fastening components and mating fastening components may be directly or indirectly attached to the outer portions of the body portions. For example, the fastening components and mating fastening components may be adhesively attached or ultra-sonic bonded to the surface of outer portion of the body portion. The first connector material may be attached to the second connector material, and the second connector material may be attached to the respective surface of the outer portion of the body portion. In this case, the first connector material will be indirectly attached to the body portion. Likewise, the second connector material may be directly or indirectly attached to the body portion.

The fastening components and mating fastening components may comprise a carrier material, onto which the first and/or second connector material is attached, the carrier material being attached to the respective outer longitudinal edge portions of the body portions. In this case, both fastening components and mating fastening components will be indirectly attached to the respective outer longitudinal edge portions of the body portions via the carrier. The carrier material may be directly or indirectly attached to the outer edge portions of the body portions of the article.

In the fastening components and mating fastening components, the first connector structure and the second connector structure may be provided by a single continuous connector material.

Such a continuous connector material will hence be provided with both first and second connector structures. The continuous connector material could be a material where the first and second structures are randomly arranged, as mentioned in the above. The continuous connector material could also be a material where the first and second structures are arranged in a selected pattern.

The first connector material, the second connector material, the carrier material, or the single continuous connector material, respectively, may be band-shaped. Provision of the connector materials as band-shaped materials may be advantageous in view of manufacturing. Such band-shaped materials could in some alternatives be arranged over the full length of the outer longitudinal edge portions of the body portions.

It has been realised, that with mechanical connectors, relatively small areas of interconnected connector structures are needed to provide sufficient connection strength. The shear force between the first connector and the second connector, when interconnected, reflects the strength of the interconnection.

Typically, each one of the refastenable side seam configurations comprises a fastening component bonded to an inner surface adjacent a distal edge of the first body portion and a mating fastening component bonded to a corresponding outer surface adjacent a distal edge of the second body portion.

According to one example embodiment, said first body portion is a front body portion and said second body portion is a rear body portion.

According to one embodiment, the length of the fastening component as seen in direction (x) is at least 75 percent of the length of the respective outer longitudinal edge portion of the body portion which it is attached, preferably at least 90 percent of said length and more preferably substantially equal to said length. Analogously, the length of the mating fastening component as seen in direction (x) is at least 75 percent of the length of the respective outer longitudinal edge portion of the body portion which it is attached, preferably at least 90 percent of said length and more preferably substantially equal to said length.

Typically, although not strictly required, the fastening component is attached to the respective body panel at a distance, b, of at least 2 mm, preferably at least 3 mm, inside the lateral side edge of said body panel. This will form a grip tab which makes it easier to open the refastenable side seam configuration.

According to one embodiment, the width in the direction (x) and the length in the direction (y) of the fastening component are substantially equal to the width in the direction (x) and the length in the direction (y) of the mating fastening component.

Pant-type absorbent articles have a defined waist opening and a pair of leg openings and are pulled onto the body of the wearer by inserting the legs into the leg openings and pulling the article up over the waist. Examples of such pant-type absorbent articles are pant diapers, sanitary pants and incontinence pants worn by incontinent adults. Pant-type absorbent articles usually comprise a front body panel and a back body panel, which are joined to each other along two opposite longitudinal side edges to define a waist-opening and a pair of leg-openings. The pant-type absorbent article further comprises a crotch portion in the part of the article that in use is intended to extend through the wearer's crotch area, between the legs. The absorbent article is intended to be placed against the skin of the wearer to absorb and contain body exudates, like urine, faeces and menstrual fluid. The disclosure mainly refers to disposable absorbent articles, which means articles that are not intended to be laundered or otherwise restored or reused as absorbent articles after use.

The term "fastening component" refers to the fastening elements that define an area of refastenable attachment. The fastening components enable refastening of the absorbent article to reconfigure the waist and leg openings into a closed configuration until the fastening components are separated. Analogously, the term "mating fastening component" refers to a fastening elements that define an area of refastenable attachment, and which configured to connect and cooperate with another fastening component. The mating fastening components enable refastening of the absorbent article to reconfigure the waist and leg openings into a closed configuration until the fastening components are separated.

Thus, the term "mating" is used herein to define a pair of fastening component arranged and configured to cooperate and connect to form a pant type configuration of the article. Accordingly, the term "mating" refers to the arrangement of the mating fastening component as seen when the article is in the closed pant-type configuration.

In the closed pant-type configuration, the edge portions of the first body portions are joined to the edge portions of the second body portions to define closed, encircled leg openings and a closed waist opening.

The term "refastenable" refers to a releasable attachment of two elements, thus the attachment may be separated and subsequently reattached without substantial permanent deformation or rupture. "Releasable attachment" refers to elements that are connected such that the elements tend to remain connected in the absence of a separation force being applied to one or both of the elements, and that the elements being capable of separation without substantial permanent deformation or rupture. The required separation force should typically be beyond that encountered while wearing the article.

The term "fixedly attached" refers to two or more elements being attached to each other so that they are not intended to be separated or disconnected during normal use of the absorbent article.

The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials. Hook fasteners are for example available from Velcro, USA.

Further features of, and advantages with, the disclosure will become apparent when studying the appended claims and the following description. The skilled person realize that different features of the disclosure may be combined to create embodiments other than those described in the following, without departing from the scope of the present disclosure.

BRIEF DESCRIPTION OF THE DRAWINGS

The present disclosure will now be further described using example embodiments as depicted in the enclosed drawings wherein.

DETAILED DESCRIPTION OF EXAMPLE EMBODIMENTS

Figure 1A:
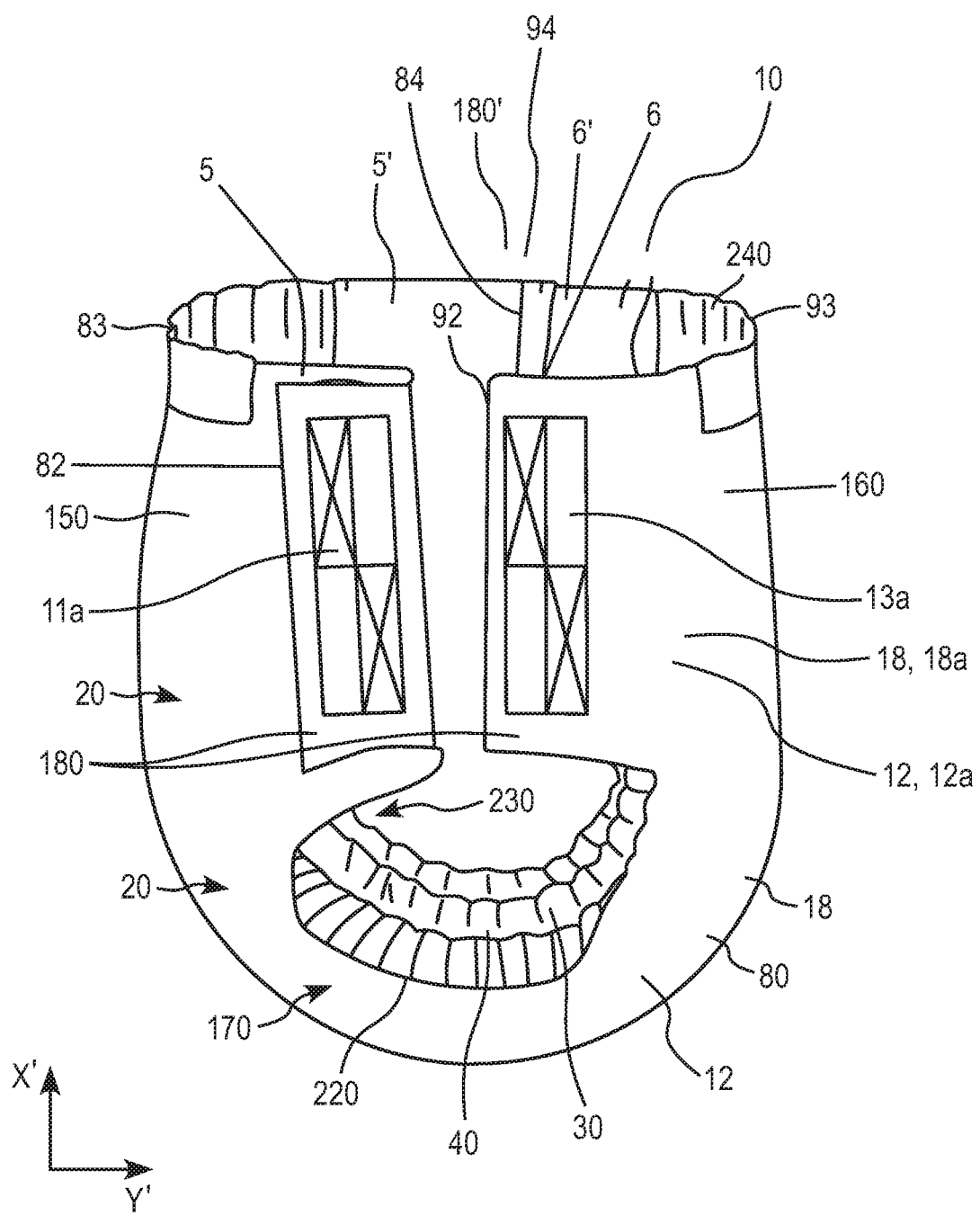
FIG. 1a shows a schematic illustration of a perspective side view of a pant-type article according to the disclosure.

The present disclosure will now be described more fully hereinafter with reference to the accompanying drawings, in which example embodiments of the disclosure are shown. The disclosure may, however, be embodied in many different forms and should not be construed as limited to the example embodiment set forth herein; rather, these embodiments are provided for thoroughness and completeness. Like reference characters refer to like elements throughout the description In FIG. 1a of the drawings an example embodiment of a disposable pant-type absorbent article 10 is schematically illustrated in an assembled and ready-to-use state. Although the following description has been made on a pant-type absorbent article in the form of a conventional pants diaper, the pant-type absorbent article may as well be provided in the form of a training pant, swim pant, sanitary pant or incontinence pant, as is readily known in the art. As used herein, "absorbent article" therefore means any article that can absorb body fluids and is suitable to be placed in close proximity to the genitals and/or anus of the user. The absorbent article is typically a disposable article. Thus, the pant-type absorbent article is typically a disposable pant-type absorbent article. However, for the sake of simplifying the description of the example embodiments, the pant-type absorbent article may sometime be denoted simply as the absorbent article or even the article.

Figures 1B, 2A:
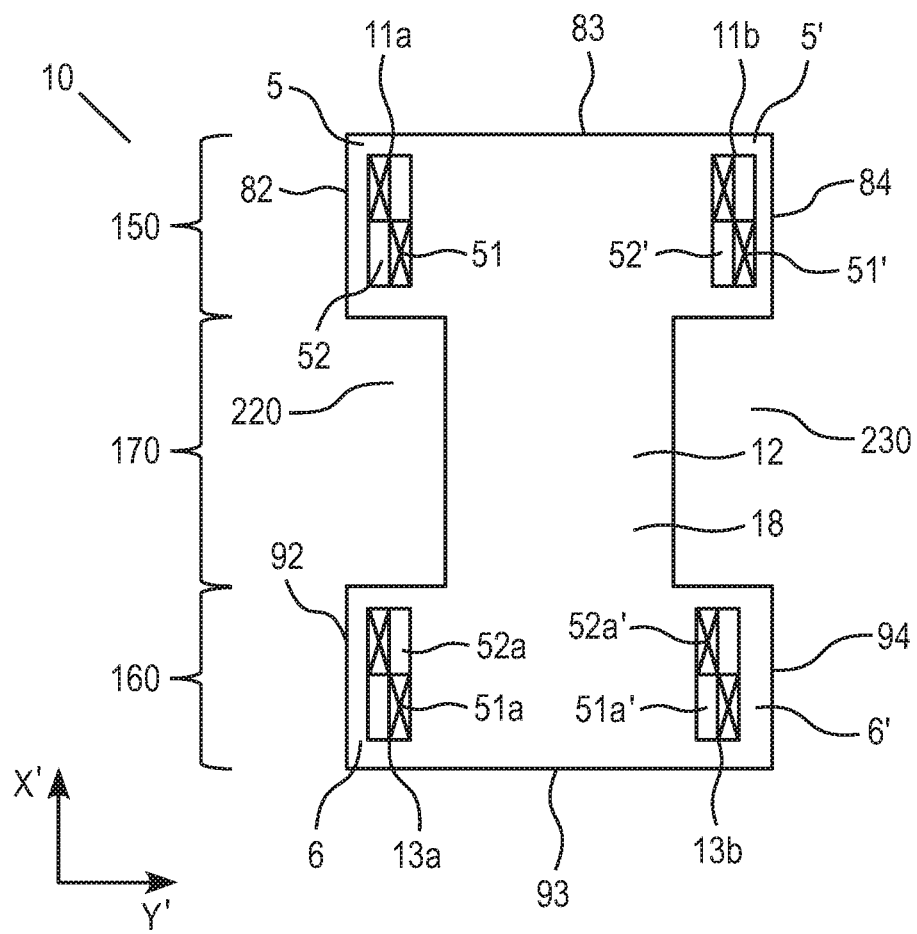
FIG. 1b shows a schematic illustration of a top view of an opened pant-type article according to the disclosure.
FIG. 2a depicts an enlarged view of a section of the article in FIGS. 1a and 1b, in which one of an outer longitudinal edge portions of a first body portion is intended to be interconnected to an outer longitudinal edge portion of a second body portion by a longitudinal refastenable side seam configuration.

Turning now to the figures and in particular to FIGS. 1a and 1b, there is depicted an example embodiment of a pant-type absorbent article in the form of a diaper for an infant or an incontinent adult. The diaper is intended to be worn around the waist of the wearer like a pair of pants. The pant-type absorbent article 10 has a longitudinal direction X', a transverse direction Y', an inner surface 12 facing the user during use, an outer surface 18 facing away from the user during use.

Further, the article 10 comprises, as seen in the longitudinal direction X' a first body portion 150, a second body portion 160 and an intermediate crotch portion 170 provided with two leg openings 220, 230.

The first body portion 150 and the second body portion 160 refer to certain areas of the article and may be continuous with and of the same material as other areas of the article or alternatively be of separate pieces of material joined to other areas of the article. The crotch portion 170 of a pant article is the part of the article that in use is intended to extend through the wearer's crotch area, between the legs. An absorbent core is typically disposed in the crotch portion and extends into the first body portion 150 and the second body portion 160. Typically, an absorbent core is disposed between an inner coversheet and an outer coversheet.

The first body portion 150 and the second body portion 160 or those parts thereof that are located outside the absorbent core region may have different material composition than the crotch portion 170. Thus according to one embodiment the areas of the first body portion 150 and the second body portion 160, which are located outside the absorbent core region may be composed of for example a laminate material having a body facing side 12a and a garment facing side 18a, while a liquid impervious outer coversheet and/or a liquid pervious inner coversheet only is present in the absorbent core region. In other embodiments the inner and outer coversheets are the same in the first body portion 150 and the second body portion 160 as well as in the crotch region 170. The first body portion 150 and the second body portion 160 each have a pair of first lateral edges 82, 92 and second lateral edges 84, 94, respectively, and a transverse edge 83 and 93, respectively.

The crotch portion 170 extends between the first body portion 150 and the second body portion 160 in the longitudinal direction X' of the article 10.

The first body portion 150 and the second body portion 160 each have a pair of outer longitudinal edge portions. Hence, the first body portion 150 has opposite defined outer longitudinal edge portions 5, 5'. The outer longitudinal edge portions 5, 5' extend essentially in the longitudinal direction X' from the leg openings to the waist opening 240, typically defined by the transverse edge 83. Thus, the outer longitudinal edge portions 5, 5' are essentially those parts of the body portion 150 that are closest to the lateral side edges, as seen in the transverse direction Y'. Analogously, the second body portion 160 has opposite defined outer longitudinal edge portions 6, 6'. The outer longitudinal edge portions 6, 6' extend essentially in the longitudinal direction X' from the leg openings to the waist opening 240, typically defined by the transverse edge 93. Thus, the outer longitudinal edge portions 6, 6' are essentially those parts of the body portion 160 that are closest to the lateral side edges, as seen in the transverse direction Y'.

The outer longitudinal edge portions 5, 5' of the first body portion 150 are adapted to be interconnected to the outer longitudinal edge portions 6, 6' of the second body portion 160 by first and second longitudinal refastenable side seam configurations 180, 180', which will be further described hereinafter.

As seen in the FIG. 1a, one of the outer longitudinal edge portions 5 of the first body portion 150 is currently non-attached to the second body 160, whilst the other outer longitudinal edge portions 5' is interconnected to the outer longitudinal edge portions 6' of the second body portion 160 by the second longitudinal refastenable side seam configurations 180, 180'.

When both outer longitudinal edge portions 5, 5' of the first body portion 150 are interconnected to the outer longitudinal edge portions 6, 6' of the second body portion 160 by first and second longitudinal refastenable side seam configurations 180, 180', the article assumes a pant-like shape having the aforementioned waist opening 240 and leg openings 220, 230.

As may be gleaned from FIG. 1a, the first refastenable side seam configuration extends from the waist opening 240 to the first leg opening (220). Analogously, the second refastenable side seam configuration extends from the waist opening 240 to the second leg opening 230.

The first and second longitudinal refastenable side seam configurations will be further explained in relation to FIG. 2a.

Depending on the type of article and type of structure, the article may comprise an outer cover assembly, a chassis or a backsheet, as is well-known in the art. As such, the first body portion 150, the second body portion 160 and the intermediate crotch portion 170 may form the outer cover assembly. Analogously, the first body portion 150, the second body portion 160 and the intermediate crotch portion 170 may form the chassis.

In various example embodiments, as seen in e.g. the FIGS. 1a-1b, the first body portion 150 is a front body portion, which in the embodiment shown in the drawings is the part of the article that in use is intended to extend over the stomach of the wearer. Analogously, the second body portion 160 is here a rear body portion, which in the shown embodiment is the part of the article that in use is intended to extend over the back of the wearer. The body portions may be parts of e.g. the outer cover assembly. However, it is also readily conceivable that the first body portion may be the rear portion and the second body portion is the front portion.

In order to facilitate the understanding of the description of the example embodiments herein, the first body portion is hereinafter denoted as the front portion, whilst the second body portion is denoted as the rear portion.
The intermediate crotch portion 170, which is normally a part of the other cover assembly, is the part of the article that in use is intended to extend through the wearer's crotch area between the legs. An absorbent core is optionally disposed in the crotch portion 170 and extends into the front and rear portions 150 and 160.

As mentioned above, the article has a longitudinal direction X' and a lateral transverse direction Y'. The absorbent article as shown in FIG. 1a may further be symmetric about a longitudinal centre axis L'. The article may be formed by the folding of a laminar structure, as is readily known in the art.

Furthermore, the article comprises longitudinal refastenable side seams configurations 180 and 180'. Typically, the side seams are formed along the laterally outermost margins of the front and rear portions 150 and 160 to thereby create a closed pants-type diaper, i.e. a unitary article having a waist opening and a pair of leg openings. The pants-type diaper is in its pant-type configuration when the first and second longitudinal refastenable side seam configurations are closed, or sealed. The first and second longitudinal refastenable side seam configurations 180, 180' are closed or sealed by a set of fastening components (fastening component and mating fastening component).

That is, each one of the refastenable side seam configurations 180, 180' comprises a fastening component 11a, 11b bonded to an outer longitudinal edge portion of the first body portion and a mating fastening component 13a, 13b bonded to a corresponding outer longitudinal edge portion of the second body portion.

Accordingly, the first refastenable side seam configuration 180 comprises a fastening component 11a bonded to an outer longitudinal edge portion 5 of the first body portion 150 and a mating fastening component 13a bonded to a corresponding outer longitudinal edge portion 6 of the second body portion 160.

Analogously, the second refastenable side seam configuration 180' comprises a fastening component 11b bonded to an outer longitudinal edge portion 5' of the first body portion 150 and a mating fastening component 13b' bonded to a corresponding outer longitudinal edge portion 6' of the second body portion 160.

In other words, at or close to the lateral side edge 82 of body portion 150, a first fastening component 11a of the first refastenable side seam configuration 180 is provided. A complementary mating fastening component 13a is provided at or close to the lateral side edge 92 of body portion 160. Analogously, at or close to the lateral side edge 82 of body portion 150, a second fastening component 11b of the second refastenable side seam configuration 180' is provided. A complementary mating fastening component 13b is provided at or close to the lateral side edge 94 of body portion 160.

Typically, although not strictly required, the fastening components 11a, 11b are bonded to the inner surface 12 of the outer longitudinal edge portion 5, 5' of the first body portion 150, whilst the mating fastening components 13a, 13b are bonded to the outer surface 18 of the outer longitudinal edge portion 6,6' of the first body portion 160. To this end, each refastenable side seam configuration forms a lap seam configuration. It should however be readily appreciated that the fastening components and the mating fastening components may be arranged vice versa, or that all of them being arranged on the inner surface 12.

When opening the article the fastening components and the mating fastening components are separated from each other and may if desired be refastened again. While it has been described and shown above that the refastenable side seam configurations are provided along both lateral sides of the pant diaper, it should be understood that only one side of the pant diaper may be provided with a refastenable side seam configuration, while the opposite side edges of the first and second body portions may be fixedly attached to each other, such as by gluing or ultrasonic welding.

In a further embodiment the front and rear portions may comprise a pair of elastic side panels, respectively. In this example embodiment, each elastic side panel of the pair of elastic side panels may constitute an outer longitudinal edge portion, respectively.

As shown in the FIGS. 1a-1b, and which is further described in relation to the other figures herein, each one of the fastening components 11a, 11b and the mating fastening components 13a, 13b comprises a first mechanical connector structure 51 and a second mechanical connector structure 52. Said first and second mechanical connector structures being two corresponding structures. Each mechanical connector structure being capable of forming a mechanical interconnection with said other mechanical connector structure, and being incapable of forming a mechanical interconnection with an identical structure, whereby corresponding fastening component and mating fastening component of one refastenable side seam configuration are mechanically connectable via said first mechanical connector structure 51 and said second mechanical connector structure 52 to form an interconnection. Hence, corresponding fastening components and mating fastening components of the refastenable side seam configurations are mechanically connectable via said first mechanical connector structures 51 and said second mechanical connector structures 52 to form an interconnection so as to form a pant-type configuration. In this context, corresponding fastening components and mating fastening components of the refastenable side seam configurations means that the first mechanical connector structure 51 of the fastening components 11a interconnects with the second mechanical connector structure 52a of the mating fastening components 13a and the second mechanical connector structure 52 of the fastening components 11a interconnects with the first mechanical connector structure 51a of the mating fastening components 13a so as to form the first refastenable side seam configuration. Analogously, the first mechanical connector structure 51' of the fastening components 11b interconnects with the second mechanical connector structure 52a' of the mating fastening components 13b and the second mechanical connector structure 52' of the fastening components 11b interconnects with the first mechanical connector structure 51a' of the mating fastening components 13b so as to form the second refastenable side seam configuration.

To this end, said first fastening component 11a is adapted to interconnect with said first mating fastening component 13a. Analogously, said first mating fastening component 13a is adapted to interconnect with said first fastening component 11a. Analogously, said second fastening component 11b is adapted to interconnect with said second mating fastening component 13b. Analogously, said second mating fastening component 13b is adapted to interconnect with said second fastening component 11b.

The fastening components can be bonded to the body portions (herein referring to the outer longitudinal edge portions) in a variety of ways known in the art, such as ultrasonic welding, adhesive or a combination thereof.

FIG. 2a depicts an enlarged view of a section of the article 10 in FIGS. 1a and 1b, more specifically one of the outer longitudinal edge portions 5 of the first body portion 150, which is intended to be interconnected to the outer longitudinal edge portion 6 of the second body portion 160 by the first longitudinal refastenable side seam configuration 180. As mentioned above, the refastenable side seam configuration comprises the fastening component 11a bonded to the outer longitudinal edge portion of the first body portion and the mating fastening component 13a bonded to the corresponding outer longitudinal edge portion of the second body portion. In other words, a refastenable side seam configuration is formed by a fastening component bonded to an outer longitudinal edge portion of a body portion and a mating fastening component bonded to a corresponding outer longitudinal edge portion of another body portion.

To this end, the article 10 illustrated in FIGS. 1a and 1b comprises the refastenable side seam configuration in FIG. 2a, in which a first fastening component 11a is arranged on the surface 12 of the outer longitudinal edge portion 5 of the body portion 150, and a mating fastening component 13a arranged on the surface 18 of the outer longitudinal edge portion 6 of the body portion 160.

The fastening components 11a, 11b and the mating fastening components 13a and 13b are mechanical connectors. Mechanical connectors have the advantage of providing a secure connection between themselves, whilst not being prone to unwanted connection to other materials. Hence, use of mechanical connectors facilitates the general fastening of side seams of the articles to maintain a pant-type configuration during use of the article.

The fastening components and the mating fastening components are thus particularly suitable for mechanically interconnecting the outer edge regions of one body portion to another body portion.

The fastening components and the mating fastening components are thus configured to allow the side seams to be openable and reclosable, which also provides the possibility of correcting the position of the outer longitudinal edge portions, if a user has unintentionally performed an unsuitable interconnection between said body portions of the article.

In the refastenable side seam configuration 180 of FIG. 2a, the fastening component 11a and the mating fastening component 13a each comprises a first mechanical connector structure 51, 51a and a second mechanical connector structure 52, 52a. The first and second mechanical connector structures 51, 51a and 52, 52a are two corresponding structures, each structure being capable of forming a mechanical interconnection with the other structure, and being incapable of forming a mechanical interconnection with an identical structure. For example, the first mechanical connection structure may be a hook connector structure, and the second mechanical connection structure may be a loop connector structure.

In other words, with respect to the fastening components 11a, said fastening component comprises a first mechanical connector structure 51 and a second mechanical connector structure 52, each mechanical connector structure being capable of forming a mechanical interconnection with said other mechanical connector structure, and being incapable of forming a mechanical interconnection with an identical structure. Analogously, with respect to the mating fastening components 13a, said mating fastening component comprises a first mechanical connector structure 51a and a second mechanical connector structure 52b, each mechanical connector structure being capable of forming a mechanical interconnection with said other mechanical connector structure, and being incapable of forming a mechanical interconnection with an identical structure.

Hereby, corresponding fastening component 11a and mating fastening component 13a of the refastenable side seam configuration 180 are mechanically connectable via said first mechanical connector structures 51, 51a and said second mechanical connectors structure 52, 52a to form an interconnection. In this context, an interconnection refers to a closed or sealed side seam configuration. Accordingly, when all corresponding fastening components and mating fastening components of the two refastenable side seam configurations are mechanically connected via said mechanical connector structures and said second mechanical connectors structure, the article is formed into its pant-type configuration.

As is described above, the first mechanical connector structure is different than the second mechanical connector structure. As an example, the first mechanical connector structure is hook and the second mechanical connector structure is a loop. Thus, the first mechanical connector structure of said fastening component is different than said second mechanical connector structure of said mating fastening component and the second mechanical connector structure of said fastening component is different than said first mechanical connector structure of said mating fastening component. As such, said first mechanical connector structure of said fastening component is adapted to interconnect with said second mechanical connector structure of said mating fastening component, and said second mechanical connector structure of said fastening component is adapted to interconnect with said first mechanical connector structure of said mating fastening component.

In some variants, said first mechanical connector structure 51 and said second mechanical connector structure 52 of said fastening component are arranged in a first pattern and the first mechanical connector structure 51a and the second mechanical connector structure 52a of said mating fastening component are arranged in a second pattern. Said first pattern and said second pattern are formed so that at least a portion of the first mechanical connector structure 51 of said fastening component mirrors at least a portion of the second mechanical connector structure 52a of said mating fastening component and at least a portion of the second mechanical connector structure 52 of said fastening component mirrors at least a portion of the first mechanical connector structure 51*a* of said mating fastening component.

In the example embodiment illustrated in FIG. 2*a*, said first mechanical connector structure 51 and said second mechanical connector structure 52 of said fastening component are arranged in a first pattern and the first mechanical connector structure 51*a* and the second mechanical connector structure 52*a* of said mating fastening component are arranged in a second pattern, said first pattern being a mirror image of said second pattern. In other words, the arrangement of the first mechanical connector structure 51 and the second mechanical connector structure 52 of said fastening component is a mirror image of the arrangement of the first mechanical connector structure 51*a* and the second mechanical connector structure 52*a* of said mating fastening component 13*a*. In this manner, the first mechanical connector structure 51 and the second mechanical connector structure 52 of the fastening component and the first mechanical connector structure 51*a* and the second mechanical connector structure 52*a* of the mating fastening component are capable of interconnecting over the entire area of the two different connector structures, thereby increasing the interconnection between the body portions to a maximum.

Accordingly, the fastening component, e.g. 11*a*, of the front body portion is mechanically connectable to the mating fastening component, e.g. 13*a*, of the rear body portion, provided said mating fastening component comprises the first and second mechanical connector structures, and provided the location of the corresponding connector structures on the respective fastening components, and the relative orientation thereof, are such that the corresponding connector structures may meet to form an interconnection.

Typically, although not strictly required, the extension and orientation of the fastening component on the outer longitudinal edge portion, as seen in the direction x' and direction y', corresponds to the extension and orientation of the mating fastening component on the other outer longitudinal edge portion, as seen in the direction x' and direction y'.

The width of the fastening component and the mating fastening component, respectively, as seen in the transverse direction y, is typically between 5 mm-40 mm. The length of the fastening component and the mating fastening component, respectively, as seen in longitudinal direction, x, is typically at least 75 percent of the length of the respective lateral edge of the body panel near which it is attached, preferably at least 90 percent of said length. It would be possible to have two or more fastening components arranged at short intervals along the respective first and second lateral edges of the body panel.

Generally speaking, the fastening component and the mating fastening component may be configured to connect at a variety of angles. While the drawings generally illustrate an essentially identical fastening component meeting with a corresponding mating fastening component, it is to be noted that the fastening component and the mating fastening component must necessarily not be identical in terms of pattern, shape and/or geometry, but that the width, length, pattern and/or shape of the fastening component may be different to the width, length, pattern and/or shape of the mating fastening component.

It is to be noted that the fastening component and the mating fastening component as described above and further described in particular with respect to FIGS. 2*a*, 3*a*-8*b* may likewise be incorporated into a mating fastening component of the refastenable side seam configuration of the article, unless explicit stated herein. In addition, any one of the example embodiments as described in FIGS. 2*a*, 3*a*-8*b* are possible to be incorporated into the absorbent article as described in relation to the FIGS. 1*a* and 1*b*, as mentioned above. Thus, it should be readily appreciated that the features, patterns, functions, examples and details of the fastening component as described in relation to the FIGS. 2*a*, 3*a*-8*b* may be installed in an article as described in relation to FIGS. 1*a*-1*b*.

In the example embodiments herein, as shown in e.g. FIG. 2*a* and FIGS. 3*a*-8*b*, it is envisaged that the fastening component and the mating fastening components 11*a*, 13*a* both comprise the first mechanical connector structure 51, 51*a* and the second mechanical connector structure 52, 52*a*, respectively.

In certain variants, the first and second mechanical connector structures 51, 52 of a fastening component may be arranged to form a pattern over a surface of the outer longitudinal edge portions 5 or 6. The example embodiments described in relation to FIGS. 3*a*-3*b*, 4*a*-4*b*, 5*a*-5*c* are all example embodiments where the first and second mechanical connector structures 51, 52 are arranged so as to form organised patterns.

In certain variants, the pattern may be adapted such that each one of the outer longitudinal edge portions 5 or 5' of the body portion 150 is mechanically connectable to each one of the outer longitudinal edge portions 6 or 6' of the body portion 160 via the fastening components and the mating fastening components. At least the variants described in FIGS. 3*a*-3*b* and 4*a*-4*b* are adapted to such use. It will be noted, that for being mechanically connectable to each one of the outer longitudinal edge portions 6 or 6' of the body portion 160 via the fastening components and the mating fastening components, there may still be requirements as to the orientation of the outer longitudinal edge portions (and the fastening components and the mating fastening components), in order to achieve such a connection.

Figure 3A:
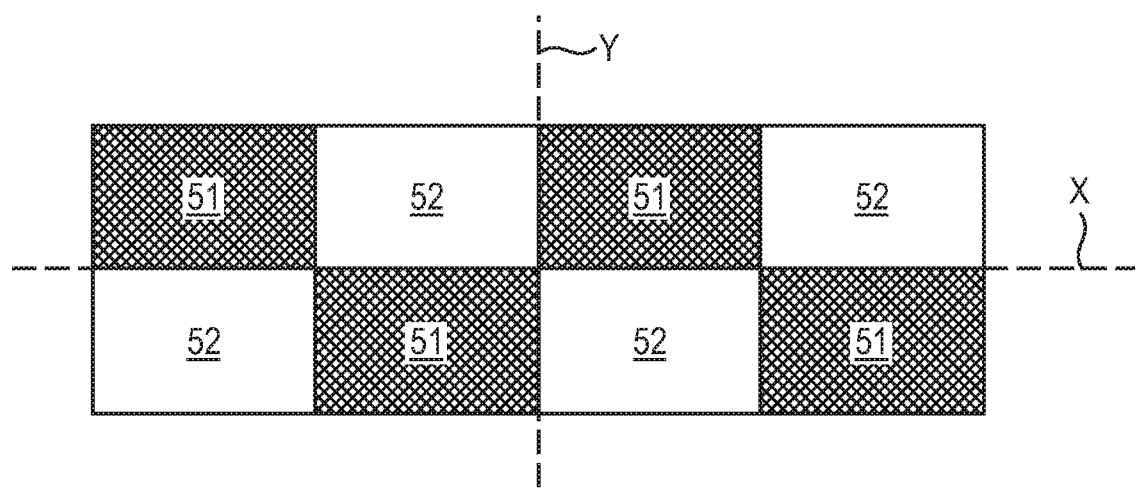
FIGS. 3a and 3b illustrate various embodiments of first and/or second connectors.
Figure 3B:
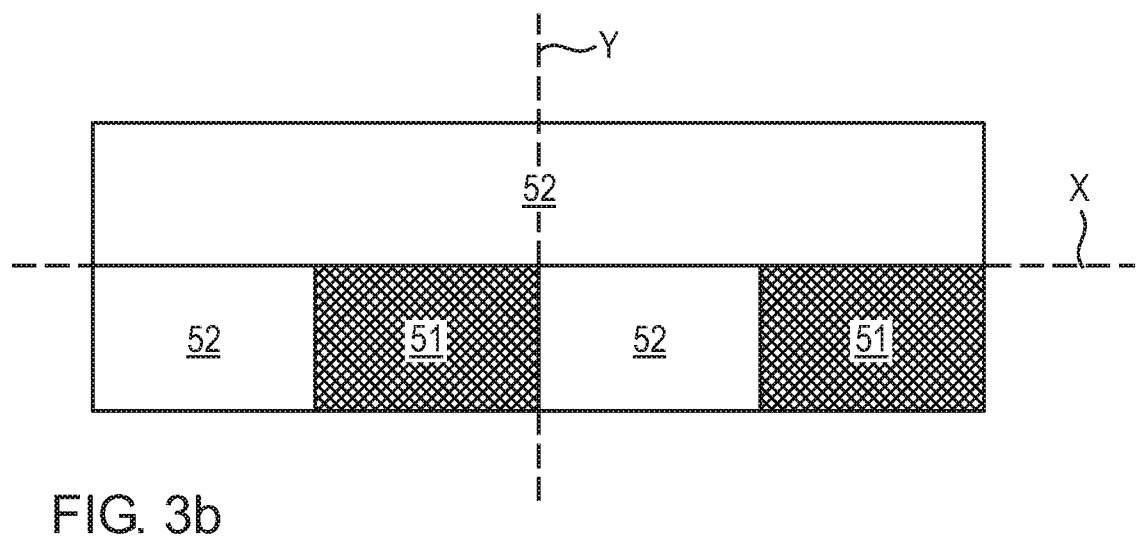

In certain variants, the pattern may be adapted such that each one of the outer longitudinal edge portions 5 or 5' of the body portion 150 is mechanically connectable to each one of the outer longitudinal edge portions 6 or 6' of the body portion 160 via the fastening components and the mating fastening components, regardless of how the respective outer longitudinal edge portions are oriented in relation to each other. In other words, the connecting system is foolproof in that all conceivable combinations when trying to set identical fastening components and mating fastening components together, will be successful. FIGS. 3*a*-3*b* illustrate a such a variant of fastening components and mating fastening components.

In FIGS. 3*a*-3*b*, FIGS. 4*a*-4*b*, and FIGS. 5*a*-5*b*, various fastening components are illustrated with reference to a longitudinal axis X and a transversal axis Y. It is to be noted, that although the figures illustrate the fastening component only, the axes are essential defined in relation to the longitudinal direction x' and the transverse direction y' of the article.

It should be readily conceivable that the description in relation to the figures mentioned above is likewise applicable to various mating fastening components of the example embodiments.

Typically, the fastening component (and mating fastening component) each defines a longitudinal central axis X extending in parallel to the length the fastening components, and centrally in relation to the width of the fastening components. Similarly, the fastening component (and mating fastening component) each defines a longitudinal transverse axis Y extending in parallel to the width of the fastening components, and centrally in relation to the length of the fastening components. The same description may also apply to the extension and direction of the outer longitudinal edge portions.

FIG. 3a illustrates a variant of a fastening component 11a where the pattern formed by the first and the second connector structures 51, 52 is asymmetrical with respect to said longitudinal central axis X, and with respect to the transversal central axis Y.

Moreover, the pattern formed by the first and second connector structures 51, 52 is such that each portion of the first structure 51 on one side of the longitudinal central axis X, mirrors a portion of the second structure 52 on the other side of the longitudinal central axis X. Similarly, each portion of the first structure 51 on one side of the longitudinal transversal axis Y, mirrors a portion of the second structure 52 on the other side of the transversal central axis Y.

This results in a "chess-board" patterned fastening component 11a as illustrated in FIG. 3a.

The arrangement with the mirroring first and second connector structures 51, 52 results in a fastening component which, when applied on both the outer longitudinal edge portions 5,6, results in a fool-proof interconnection (closed refastenable side seam configuration) of said body portions. No matter in which orientation the connectors are situated when they meet each other, each portion of the first structure 51 will always meet a portion of the second structure 52, resulting in an interconnection between said portions. Hence, the likelihood of an interconnection being created, if two such outer longitudinal edge portions are randomly put together, is 100%.

FIG. 3b illustrates another variant of a fastening component 11a, where the pattern formed by the first and the second connector structures 51, 52 is asymmetrical with respect to said longitudinal central axis X, and with respect to the transversal central axis Y.

In this case, on one side of the longitudinal central axis X only the second connector structures 52 appears. On the other side of the longitudinal central axis X, there is a pattern comprising portions of the first connector structure 51, and of the second connector structure 52, arranged in an alternating manner and mirroring each other as seen over the transversal axis Y.

In the illustrated arrangement, each portion of the first structure 51 on one side of the longitudinal central axis X, mirrors a portion of the second structure 52 on the other side of the longitudinal central axis X. Similarly, each portion of the first structure 51 on one side of the longitudinal transversal axis Y, mirrors a portion of the second structure 52 on the other side of the transversal central axis Y. Accordingly, also the fastening component illustrated in FIG. 3b results in a fool-proof interconnection between fastening components provided with such connectors on both of their portions 5,6. No matter in which orientation the fastening component and the mating fastening component are when they meet each other, some portion of the first structure 51 of the fastening component will always meet a portion of the second structure 52 of the mating fastening component, and result in an interconnection. Hence, the likelihood of an interconnection being created, if two such outer longitudinal edge portions are randomly put together, is 100%.

In the embodiment illustrated in FIG. 3b, all portions of the first mechanical connector structure 51 may not meet a portion of the second mechanical connector structure 52 in all possible relative orientations of the fastening component and the mating fastening component. This is, however, not required for ensuring connection between the fastening component and the mating fastening component. Accordingly, the arrangement illustrated in FIG. 3b might be perceived as a simplified variant of the arrangement of FIG. 3a.

Indeed, in order to provide at least one portion of the first structure 51, located on one side of the longitudinal central axis X and on one side of the transversal central axis Y; mirroring a portion of the second structure 52 on the other side of the longitudinal central axis X and another portion of the second structure 52 on the other side of the transversal central axis Y, so as to render the connection between two such fastening component and mating fastening component fool-proof, it would be sufficient to provide a fastening component similar to the one illustrated in FIG. 3b, but comprising only one single portion of the first structure 51.

Figure 4A:
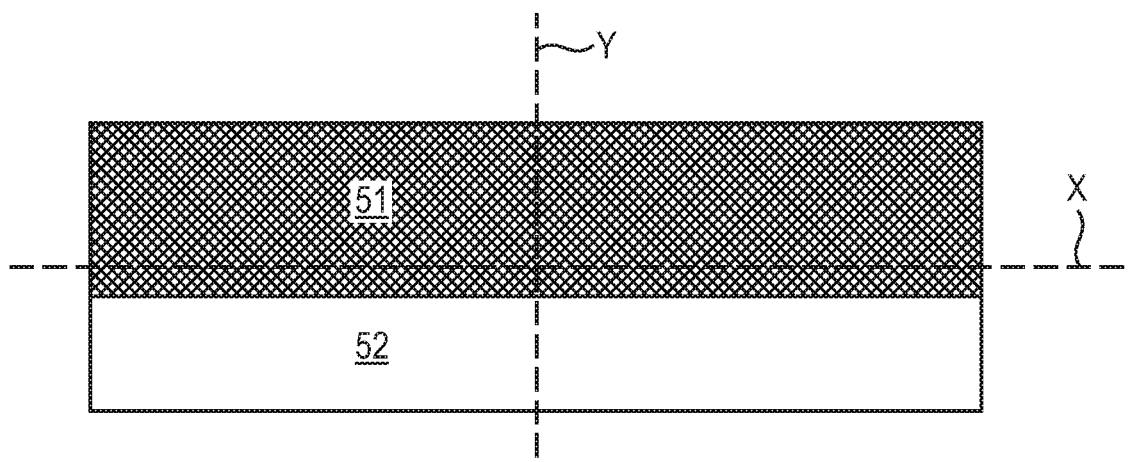
FIGS. 4a and 4b illustrate various embodiments of first and/or second connectors.

FIG. 4a illustrates an example of a fastening component where a first mechanical connector structure 51 and a second mechanical connector structure 52 are asymmetrically arranged with respect to the longitudinal axes X, but symmetrically arranged with respect to the transversal axes Y. Analogously, FIG. 4a may illustrate an example of a mating fastening component where a first mechanical connector structure 51a and a second mechanical connector structure 52b are asymmetrically arranged with respect to the longitudinal axes X, but symmetrically arranged with respect to the transversal axes Y.

Although such arrangements will generally provide less versatility as to the interconnection between the fastening component and the mating fastening component, they may nevertheless contribute to an ease of manufacturing.

The example embodiment of a fastening component in FIG. 4a comprises a portion of the first connector structure 51, which extends on one side of the longitudinal axis X, and slightly over said axis X. A portion of the second connector structure 52 is hence arranged at a distance from the longitudinal axis X, and extending further away from the longitudinal axis X. The portions of the first and the second connector structure 51, 52 both extend in a band-shaped manner along the longitudinal axis X.

A fastening component as illustrated in FIG. 4a may be mechanically connected to an identical mating fastening component, if the identical fastening component and mating fastening component are positioned in relation to each other such that the first connector structure 51 of the fastening component meets the second connector structure 52 of the mating fastening component. Hence, refastenable side seam configurations comprising identical such fastening components on both portions 5,6 would, if randomly oriented, display a likelihood of becoming interconnected of 50%

Figure 4B:
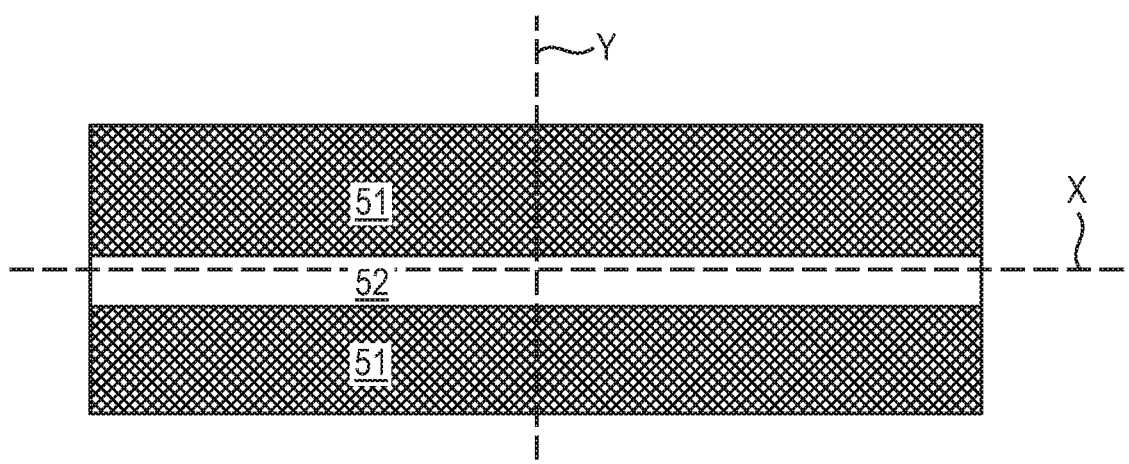
Figure 5A:
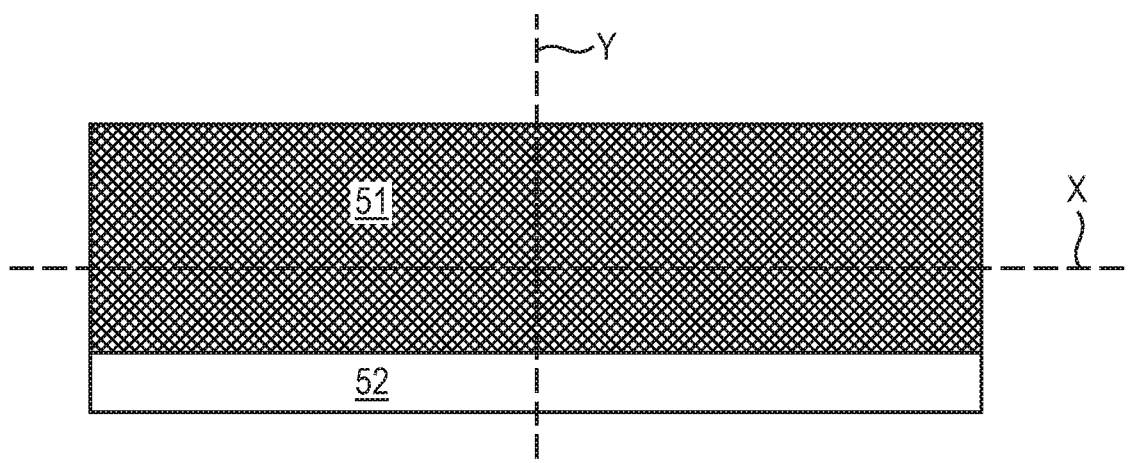
FIGS. 5a to 5d illustrate various embodiments of first and/or second connectors.
Figure 5B:
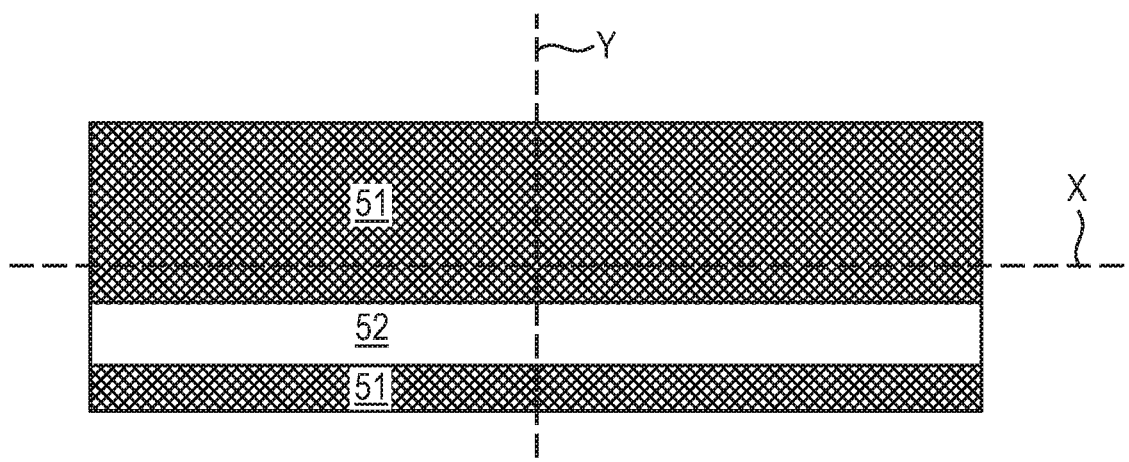
Figure 5C:
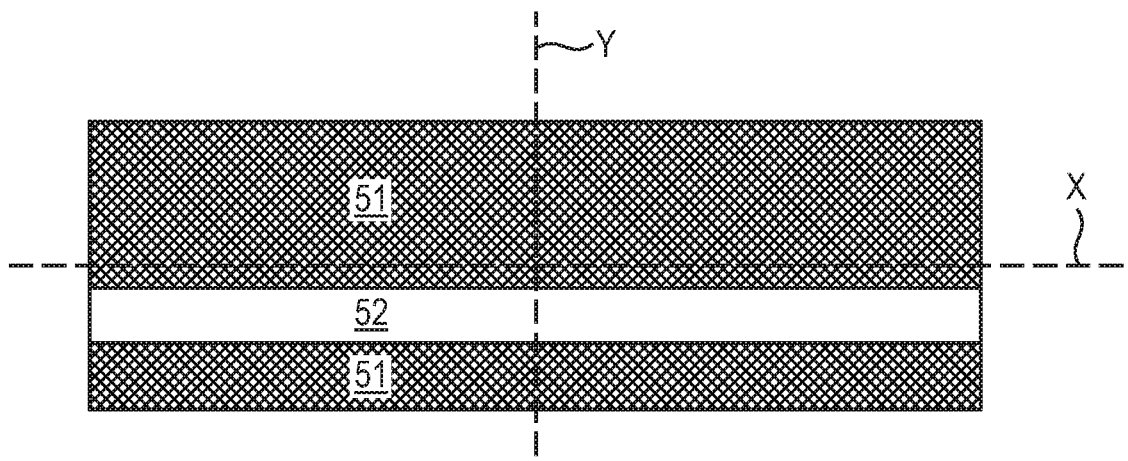
Figure 5D:
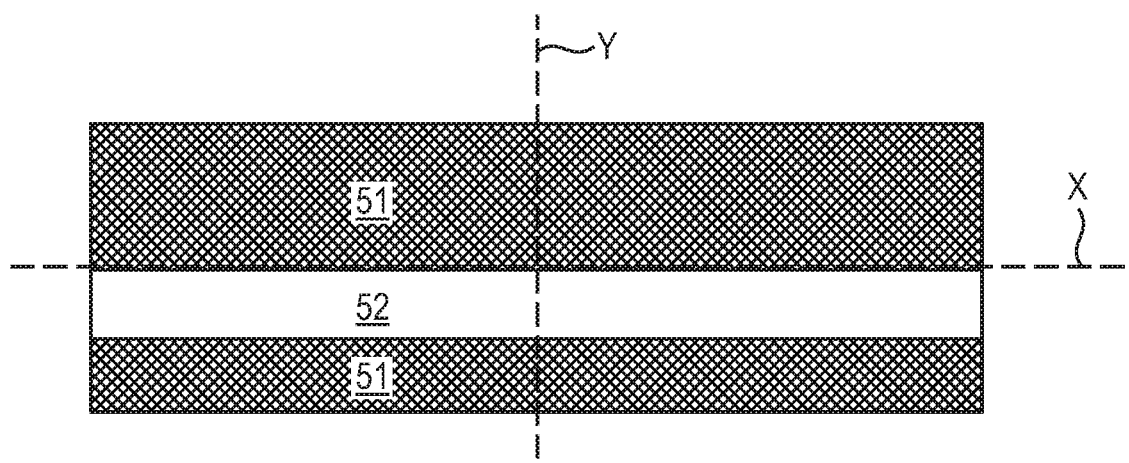

However, the embodiment of a fastening component in FIG. 4a may be used together with another mating fastening component, e.g. as illustrated in FIG. 4b, to facilitate interconnections of the refastenable side seam configuration. The fastening component as illustrated in FIG. 4b comprises two portions of the first connector structure 51, extending along the longitudinal axis X. A portion of the second connector structure 52 is further arranged in between the two portions of the first connector structure 51.

The second connector structure 52 of the fastening component of FIG. 4b is arranged in a staggered relationship to the second connector structure 52 of the mating fastening component in FIG. 4a. Accordingly, a fastening component in accordance with FIG. 4b will be connectable to a mating fastening component in accordance with FIG. 4a, regardless of how the fastening component and the mating fastening component are oriented in relation to each other.

Accordingly, a refastenable side seam configuration may be provided with a fastening component 11a on an outer edge portion 5, which is in accordance with FIG. 4a, and with a fastening component 13a on an outer edge portion 6, which is accordance with FIG. 4b. In this case, the likelihood of achieving an interconnection between two outer edge portion 5,6 of a fastening component and a mating fastening component, when no concern is taken to the relative orientation of the components may be about 75%.

As understood by the examples of FIGS. 3a-3b, and FIGS. 4a-4b, various designs and example embodiments of the fastening components and the mating fastening components intended for interconnection with each other via first and second mechanical connectors provided on each fastening component and mating fastening component may be provided such that the first and second mechanical connectors of the fastening component is mechanically connectable to the first and second mechanical connectors of the mating fastening component.

In this case, the first and second mechanical connectors of each fastening component and mating fastening component may also be identical. Alternatively, the first and second connector of each fastening component and mating fastening component may be different.

Another option is to provide each fastening component and mating fastening component having first and second mechanical connectors, where the appearance of the first and/or second mechanical connector may differ between the fastening components of one body portion and the mating fastening components of another body portion.

For example, the fastening component of one body portion may display a first pattern, whilst the mating fastening component of another body portion may display a second pattern. In this case, the connection possibilities between the fastening component and mating fastening component might be different, whilst still providing a sufficient level of connection strength. Nevertheless, by selecting suitable patterns, and suitable variations between patterns, it may be ensured that a sufficient number of connection possibilities is obtained.

FIGS. 5a to 5d illustrate some variants of the fastening component and the mating fastening component that may be used for such embodiments. In these variants, a fastening component 11a is symmetrically arranged in view of the longitudinal and transversal axis X, Y. A first connector structure 51 extends over the entire area spanned by the fastening component 11a, apart from over a band shaped area extending along the transversal axis X, and which is occupied by a second connector structure 52. From FIGS. 5a-5d, it may be seen how the location of the band-shaped area of the second connector structure 52 varies between the variants of the figures, in that the distance between the band-shaped area of the second connector structure 52 and the transversal axis X varies. The area comprising the second connector structure 52 may be described as "wandering" over the area of the fastening component 11a.

To this end, as shown by the example embodiments, the fastening component and mating fastening component will always be connectable to each other, regardless of the orientation of said fastening component and said mating fastening component. However, if the fastening component is to be connected to another, identical mating fastening component, there is a risk that no connection will occur, should two identical components meet when identically orientated.

In the embodiments described in relation to FIGS. 5a-5d, the different patterns of the fastening component and mating fastening component are obtained by varying a selected pattern in a controlled manner. Such variations may result e.g. if using a continuous connector material displaying a repeated pattern for forming the fastening component and mating fastening component, and where the pattern repetition is not evenly divisible with the selected component length. In this case, for each fastening component and mating fastening component cut from the connector material, the pattern will "wander" a distance corresponding to the mismatch between the pattern repetition length and the component length.

Other embodiments are possible where the fastening component and mating fastening component are provided with randomly selected or varied patterns.

To provide the fastening component and the mating fastening component 11a, 13a on the outer longitudinal edge portions 5, 6 of the body portions, numerous alternatives are possible.

For example, the first connector structure 51 may be provided by a first connector material 51', and the other connector structure is provided by a second connector material 52'.

Figure 6A:
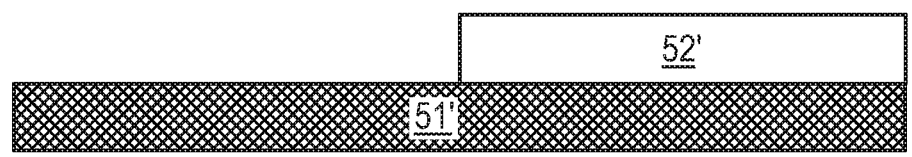
FIGS. 6a to 6c illustrate various embodiments of first and/or second connectors.
Figure 6B:
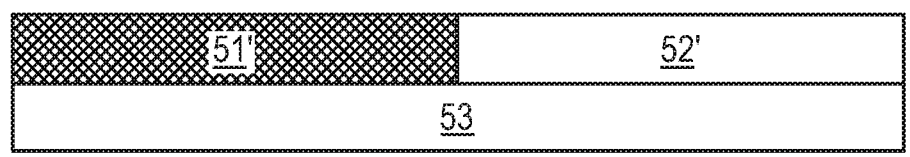
Figure 6C:
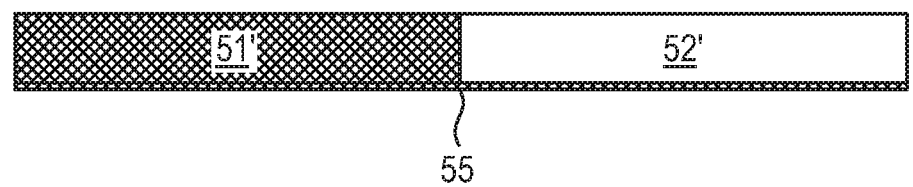

FIGS. 6a to 6c illustrate various variants of fastening components and mating fastening components, viewed in a cross-section along the axis Y.

FIG. 6a illustrates a variant wherein the second connector material 52' is attached to the fist connector material 51'. The first connector material 51' may then be attached to the respective portion 5, 6 of the body portions by adhesive, ultra-sonic welding or the like.

Using this variant, a variant of a fastening component or mating fastening component such as the one illustrated in FIG. 3a or 3b may be manufactured by attachment of intermittent pieces of second connector material 52' onto a continuous piece of first connector material 51'.

In another variant, a first connector material 51' may be provided as a continuous piece of material. A second connector material 52' may be provided as a piece of material in which through holes are formed. The second connector material 52' may then be applied over the first connector material 51', such that the first connector structures 51 of the first connector material 51' is accessible via the through holes in the second connector material 52'. The first connector material 51' may then be attached to the respective outer longitudinal edge portion of the body portion.

For example, in accordance with the last mentioned variant, a continuous piece of second connector material 52', in which through holes are cut out, may be laminated over a continuous piece of first connector material 51', resulting in a continuous piece of connector material comprising first mechanical connector structures 51 and second mechanical connector structures 52, which may be used to form fastening components and mating fastening components 11a, 11b, 13a, 13b. The first connector material 51' may in this case be a loop material, and the second connector material 52' may be a hook material.

In the above-mentioned example, the through holes may be cut out randomly, so as to provide different fastening component or mating fastening component displaying random variations.

Alternatively, the through holes may be cut out in a selected pattern. A connector material comprising a selected pattern may be used for forming identical fastening component and mating fastening component (e.g. if the pattern repetition is evenly divisible with the length of the fastening component and mating fastening component), or different fastening component and mating fastening component (e.g. if the pattern repetition is not evenly divisible with the length of the fastening component and mating fastening component).

FIG. 6b illustrates a variant wherein the fastening component 11a comprises a carrier material 53, onto which said first and second connector material 51', 52' is attached. The carrier material 53 is typically attachable to the respective outer longitudinal edge portions 5, 6 of the body portions.

The variants exemplified by FIGS. 6a and 6b may be formed directly on the outer longitudinal edge portions 5, 6 of the body portions, after manufacture thereof.

FIG. 6c illustrates an embodiment of a fastening component, wherein the first mechanical connector structure 51 and the second mechanical connector structure 52 is provided by a single continuous connector material. Such a material may comprise a backing 55 from which the mechanical connectors structures 51, 52 extend.

In the examples of FIGS. 6a to 6c, the fastening component is illustrated as a unitary fastening component, forming a continuous piece of material which may be attached to the outer longitudinal edge portion 5 or 6 of the body portion. Naturally, other variants of unitary fastening components are conceivable.

However, a fastening component may also be formed by attachment of one or several separate material pieces of connector structure material intermittently arranged on the outer longitudinal edge portion 5 or 6 of the body portion. In this case, the fastening component may be described as an intermittent fastening component. Analogously, a mating fastening component may also be formed by attachment of one or several separate material pieces of connector structure material intermittently arranged on the mating outer longitudinal edge portion of the body portion. In this case, the mating fastening component may be described as an intermittent mating fastening component.

Furthermore, according to some variants, each one of the refastenable side seam configurations may comprise a set of fastening components bonded to an outer longitudinal edge portion of the first body portion. The set of the fastening components typically comprise a plurality of fastening components arranged spaced apart as seen in the longitudinal direction. In addition, or alternatively, the plurality of fastening components may be arranged spaced apart as seen in the transverse direction.

Analogously, each one of the refastenable side seam configurations may comprise a set of mating fastening components bonded to a corresponding outer longitudinal edge portion of the second body portion. The set of the mating fastening components typically comprise a plurality of mating fastening components arranged spaced apart as seen in the longitudinal direction. In addition, or alternatively, the plurality of mating fastening components may be arranged spaced apart as seen in the transverse direction.

Figure 7A:
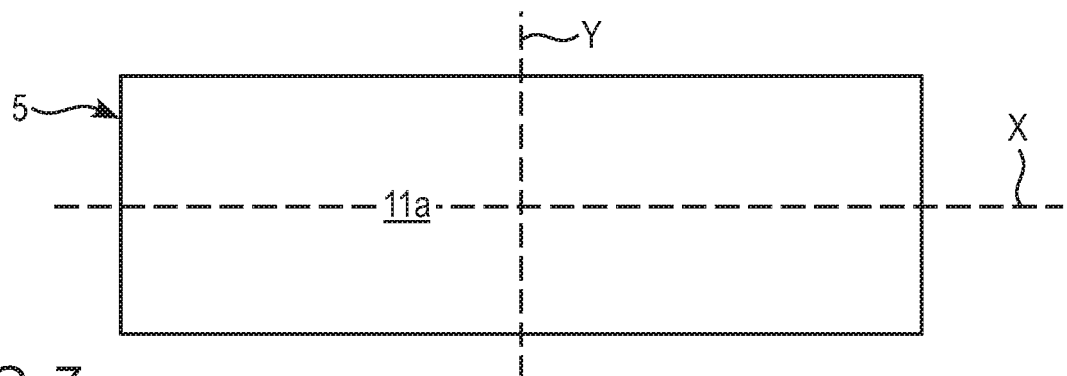
FIGS. 7a to 7c illustrate various embodiments of body portion surfaces comprising connectors.

As illustrated by FIG. 7a, the fastening component 11a may be arranged so as to extend over essentially the entire outer longitudinal edge portion 5. It should be noted that the FIGS. 7a-7c merely shows a cut-out view of the outer longitudinal edge portion of the body portion of the article so as to simplify the description and illustration of the various variants.

If the fastening component is a unitary fastening component, e.g. in accordance with the examples of FIGS. 6a to 6c, this means that the entire body portion surface at the outer longitudinal edge portion 5 will be covered by the fastening component 11a. If the fastening component 11a comprises several separate material pieces, the body portion surface (the web material) at the outer longitudinal edge portion 5 may be visible between the separate material pieces of connector structure.

Alternatively, the fastening component may extend over only a portion of the length L or width W of the outer longitudinal edge portion.

Figure 7B:
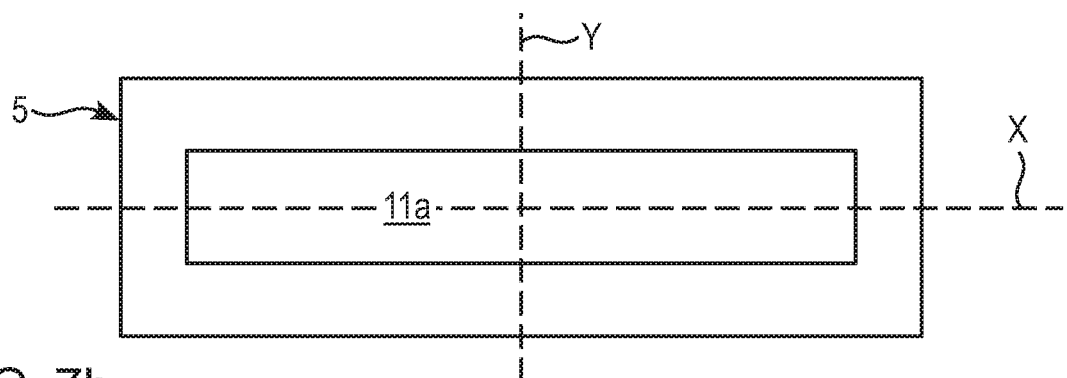

FIG. 7b illustrates an arrangement where the fastening component 11a extends over only a portion of the length L and over only a portion of the width W of the outer longitudinal edge portion 5. In this case, the fastening component 11a is centrally arranged in view of said width and length (and consequently in view of said longitudinal and transverse axis X, Y).

Figure 7C:
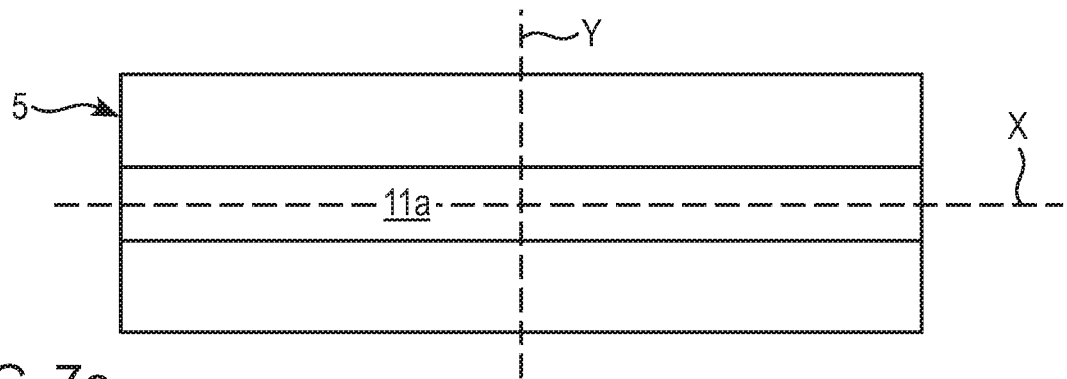

FIG. 7c illustrates an arrangement where the fastening component 11a extends over the entire length L, but only over a portion of the width W of the outer longitudinal edge portion 5. The fastening component 11a is centrally arranged in view of said width and length (and consequently in view of said longitudinal and transverse axis X, Y).

Central arrangement of the fastening component on the end surface of the body portion, i.e. the outer longitudinal edge portion, may be used to ensure that the fastening component arranged on an outer longitudinal edge portion of one body portion and the mating fastening component arranged on an outer longitudinal edge portion of the other body portion will meet in a controlled manner. In this case, any desired asymmetry of the first and/or second surface structure in relation to the longitudinal and/or transversal axis is obtained by the arrangement of the surface structures in relation to the fastening component.

However, variants are conceivable wherein any desired asymmetry of the first and/or second surface structure in relation to the longitudinal and/or transversal axis is at least partly obtained by asymmetrical arrangement of the fastening component on the outer longitudinal edge portion of the body portion.

The attachment of the fastening component 11a to an outer longitudinal edge portion 5 of a body portion may be performed directly or indirectly. Advantageously, the attachment may be an adhesive attachment, performed e.g. by gluing, or by the provision of the fastening component as an adhesive sticker. Alternatively, the attachment of the fastening component to an outer longitudinal edge portion may be performed by ultra-sonic welding to form an ultra-sonic bond.

The fastening component 11a and the mating fastening component 13a may each have a height of less than 2 mm, preferably less than 1 mm, most preferred 0.6 mm. The height is to include the entire connector, including e.g. backing materials etc.

The shear force between the fastening component and the mating fastening component, when interconnected, reflects the strength of the interconnection. The fastening component and the mating fastening component should be selected such that, when connected, the interconnection is able to resist the forces involved when the article is to be used in its pant-type configuration.

It is understood, that the various examples of the refastenable side seam configurations, the fastening components and the mating fastening components may be combined with each other and/or with features described in relation to any one of the examples.

If desired, the pattern formed by the first mechanical connector structure and the second mechanical connector structure may be used as a visual indicia for indicating a correct fastening so as to form a comfortable and secure closed refastenable side seam configuration during use of the article. Such an indicia may be useful in particular when the article and its fastening components and mating fastening components are adapted so as to provide a higher likelihood of interconnection.

The various fastening components and mating fastening components proposed herein are particularly useful for reclosable absorbent articles such as reclosable pant-type absorbent articles having a set of refastenable side seam configurations being designed to allow a user or caregiver to open and reclose the article as desired.

In view of the above disclosure explaining how to provide fastening components and mating fastening components for achieving an interconnection between body portions of the article, it will be understood that the article is provided with improved refastenable side seam configuration in terms of secureness and ease of handling. In particular, as described above in relation to the figures, the mechanical interconnection provided by having two types of mechanical connector structures on each fastening component and mating fastening component contributes to minimize the risks of having a poor fastening of the pant-type absorbent article around the wearer during use. As a poor fastening often results in a poor fit of the article and an increased risk of leakage, the example embodiments of the disclosure may also have a positive impact on overall fit of the article, whilst reducing the risk of leakage during use of the article. Due to that each one of the fastening components and the mating fastening components comprising both first mechanical connector structure and second mechanical connector structure, the peel strength and shear strength of the refastenable side seam configuration, when sealed, is further improved as the number and type of connection areas of the seam is increased in view of known side seam configuration having a fastening component comprising a hook material and a mating fastening component comprising a loop material.

Different patterns formed by the first and second connector structures in order to provide a suitable fastening component may be designed, and such patterns may be combined in different manners. Although several of the patterns given in the illustrated examples display continuous rectangular areas comprising the first or the second connector structures, patterns may naturally be formed by other intermittent or continuous areas, having any desired shape, e.g. circular, triangular, half circular or the like.

Figure 8A:
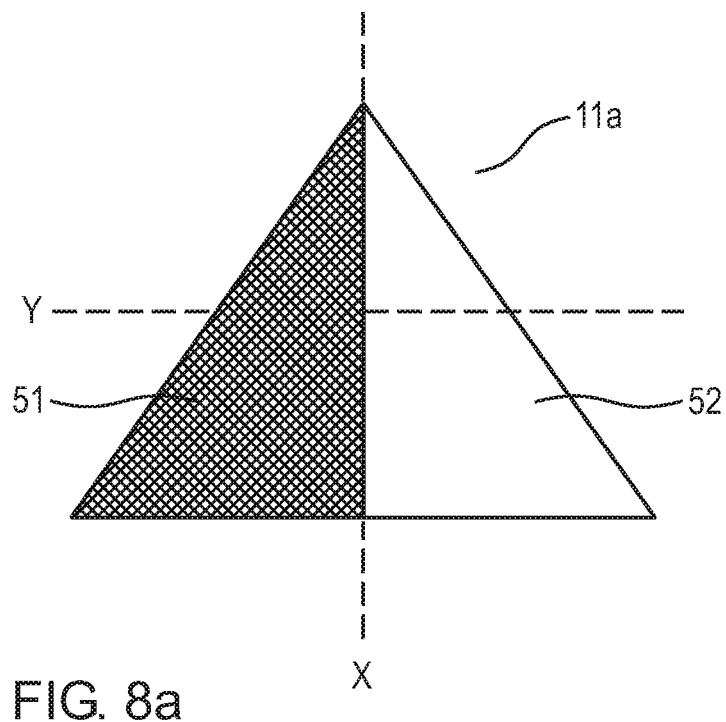
FIGS. 8a and 8b illustrate further embodiments of first and/or second connectors.

As an example, FIG. 8a illustrates one example embodiment of a fastening component in the shape of a triangle, in which the first and second mechanical connector structures 51, 52 are provided as right angled triangles, respectively.

Figure 8B:
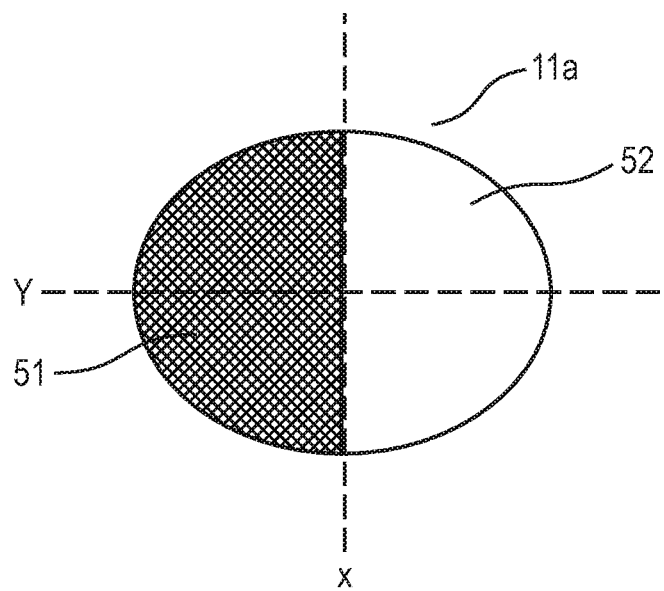

FIG. 8b illustrates another example embodiment of a fastening component in the shape of a circle, in which the first and second mechanical connector structures 51, 52 are provided as half circles, respectively. It should be readily appreciated that the shapes illustrated in FIGS. 8a and 8b may also be used as the shape of the mating fastening component. Accordingly, it is to be noted that the fastening component and the mating fastening components, as well as the pattern of the mechanical connectors may be provided in several different forms and shapes depending on the design, use and function of the article.

The nonwoven material layers or webs of the present disclosure forming the chassis may for example be selected from, for example, of spunbond, air laid, wet laid, carded, electro spunned or meltblown nonwovens. The nonwoven material may be bonded by multiple techniques, e.g. by needling, hydroentangling, or heat bonding. The nonwoven material of the disclosed products is a mixture of natural and synthetic materials. Natural fibres are for instance cellulosic fibres or fibres from regenerated cellulose.

In all example embodiments of the disclosure, as described herein, it is to be noted that the article 10 typically further comprises an inner topsheet (not shown in FIG. 1a). The topsheet is that sheet which in use of the diaper is in contact with the skin of the wearer or at least facing the skin. The article may also be provided with a waist containment pocket and elasticised leg openings, i.e. leg opening, leg opening, leg elastics and leg elastic. Since such constructional features are, however, well known in the art, they will not be described in further detail. The article may also be provided by a so-called raised barrier cuffs {not shown) in order to provide an improved security against leakage. These raised barrier cuffs may in some instance replace leg elastics.

In another alternative embodiment of a diaper structure, side panels, normally of an elasticized material, may be provided on the front and rear portions to form a more comfortable waist opening. Each side panel is made up of a first side panel portion adjacent the front portion and a second side panel portion adjacent the rear portion. Each side panel may have a fastening means, for example a mechanical fastening means, in the form of a hook or loop member, intended to cooperate with a complementary mechanical fastening means on the outside of the front portion, the so-called landing zone.

Typically, the entire external surface of the outer cover assembly of the front panel may comprise a non-woven material, which functions as a loop material or a separate strip of loop material may be attached to the external surface of the front panel forming the landing zone.

The materials making up the diaper 10 may be selected from any of the materials commonly used for such products and may include environmentally friendly materials from renewable sources and/or biodegradable material. As an example, the topsheet, i.e. the liquid permeable layer may suitably be made of a non-woven material. Another conceivable material is perforated plastic. In particular, the material of the top sheet is preferably selected from a material that exhibits characteristics such as dryness and softness when the diaper is being worn. Such top sheets are conventionally known in the art, and may be used without particular limitation, as circumstances dictate. The absorbent core 40 is normally enclosed between the liquid permeable topsheet and a liquid impermeable outer cover assembly. The absorbent core 40 may extend between the front portion 150 and the rear portion 160 in the longitudinal direction X of the disposable absorbent article 10 and be joined to the front and rear portions 150, 160. However, the absorbent core 40 may only be joined to one of the front and rear portions 150, 160, or solely to the crotch portion 170, as desired. Suitably, at least the crotch portion 170 extends between the front portion 150 and the rear portion 160. However, if no crotch portion 170 is present, the absorbent core must extend between the front portion 150 and the rear portion 160 and be joined thereto. The absorbent core 40 can be of any conventional kind.

Examples of commonly occurring absorbent materials are cellulosic fluff pulp, tissue layers, highly absorbent polymers (so-called superabsorbent polymers, or SAP), absorbent foam materials, absorbent nonwoven materials or the like, and mixtures and/or laminates thereof, compressed or uncompressed, as requirements dictate. Further, the size and absorbent capacity of the absorbent core may be varied to be suited for different uses such as for infants or for incontinent adults. Beside the absorbent core, the diaper may also comprise other layers such as a fluid acquisition layer for a quick transport of body fluids. The fluid acquisition layer has an open porous structure and should be able to quickly receive and temporarily store a certain amount of fluid and transfer it further to the underlying absorbent core. The outer cover assembly 20 may e.g. comprise at least a first nonwoven layer and an inner liquid-impermeable film layer (not shown). The outer cover assembly 20 may also be referred to as a multi-component outer cover, chassis or backsheet. The outer cover assembly, in use, covers the absorbent core 40 on the garment-facing side thereof. The topsheet 30 and outer cover assembly 20 generally have a similar extension in the plane, while the absorbent core 40 has an extension which is somewhat smaller. The topsheet 30 and outer cover assembly 20 are joined to one another around the periphery of the absorbent core, so that the absorbent core is enclosed within the envelope formed by the topsheet 30 and cuter cover assembly 20. The topsheet 30 and outer cover assembly 20 may be joined to one another by any means common in the art, e.g. ultrasonic welding, thermal welding or gluing.

The outer cover assembly material may be breathable so as to allow vapour to escape from the absorbent core while still preventing liquids from passing therethrough. Examples of breathable materials are microporous polymeric films, nonwoven laminates from spunbond and meltblown layers, laminates from microporous polymeric films and nonwoven materials. The areas of the outer cover assembly 20 outside of the absorbent core 40 may be formed of the topsheet and the outer cover assembly joined together to form a laminate structure. Alternatively at least part of the outer cover assembly outside the absorbent core area is made of another web material, which provides comfort and breathability. As mentioned above, the outer cover assembly 20 may comprises a liquid impervious film layer 80, such as a thin plastic film, e.g. a polyethylene or polypropylene film. The liquid impervious film layer should at least cover the absorbent core on the garment-facing side thereof. The liquid impervious film layer may also be breathable. This allows a higher degree of comfort for the wearer, as moisture/humidity build-up is reduced or completely avoided.

The outer cover assembly 20 further comprises a first nonwoven layer. As the outer cover assembly 20 is exposed to the outside of the pant diaper in the crotch portion 170 and may come into contact with a wearer's skin when the diaper is worn, the first nonwoven layer preferably has a textile or textile-like outer surface in order to avoid the stickiness that may be felt in contact with a plastic film surface. A textile or textile-like outer surface is also preferred for the reason that it enhances the likeness of the pant diaper or other pant garments to regular underwear. The first nonwoven layer is preferably a spunbond, meltblown, spunlaced, hydroentangled, wetlaid or carded bonded nonwoven. The fibres of the nonwoven material may be natural (e.g. rayon or cellulose fibres) or artificial (e.g. polymeric fibres such as polyolefin fibres, e.g. polyethylene or polypropylene fibres). The first nonwoven layer may be elastic or inelastic and will preferably comprise or consist of at least one nonwoven ply. The first nonwoven layer may even comprise a laminate of two or more nonwoven plies, such as a SMS (Spunbond-Meltblown-Spunbond)-composite material. The first nonwoven layer may form part of a chassis for a disposable pant-type garment. The first nonwoven layer should suitably be air-permeable. In order to ensure a high degree of leakage security, the absorbent articles are preferably designed to closely fit the body of the user in such a way that the absorbent articles do not become loose or slip off the body of the user.

The outer cover assembly 20 can for instance be provided with a number of elastic threads arranged parallel from the waist opening 240. The elastic threads are preferably also arranged towards the leg openings 220 and 230, as previously explained. In this manner, the absorbent article is provided with a more comfortable fit allowing good leakage security. Thus, in some example embodiments, a plurality of elastic members, together forming the so-called waist elastic, may be fixedly disposed over the width of the outer cover assembly 20 in their tensioned state such that they can contract and thus gather the nonwoven material in the waist band when they are allowed to relax. An embodiment of a disposable pant diaper need not have waist elastic with the configuration shown in FIG. 1a. The waist elastic may be entirely absent or may be arranged on only one of the front portion 150 and the rear portion 160. The waist elastic may extend along only a part of the waist opening 240 such as along a central section of the front waist edge and/or the rear waist edge. The outer cover assembly 20 is preferably inelastic in the crotch area. The outer cover assembly may further comprise body elastic. The body elastic may be integrated with one of several material layers of the body portions, for example as elastic elements extending through the layer, such that the outer cover assembly is elasticated. The elastic members may be elastic strings or bands that may be uniformly or non-uniformly spaced over the portions 150 and 160 and that may have been applied with the same or different tensioning. The body elastic is not essential, however, and may be omitted or designed in other ways as found suitable for a specific purpose, Accordingly, body elastic may be applied to only one of the front and rear body portion 150 and 160 and may include or consist of curved elastic elements. The body elastic may extend over part of the absorbent core. However, in order to prevent the absorbent core from being puckered when the outer cover assembly of the absorbent article is elasticated, it is common to allow the elastic threads, or the elastic material, to extend only over the upper portions of the absorbent article. Hence the elastic threads typically only extend from the waist opening to the absorbent core, but not over the absorbent core.

In an alternative example, the front portion and the rear portion (or the outer cover assembly) are provided with an elastic film material (not shown) such that the outer cover assembly is elasticated.

As mentioned above, a major part of the front and back portions 150 and 160 may alternatively be made of an inelastic material and elasticized side panels may be provided in the sides of the absorbent article in the area bridging the front and back portions.

The term "nonwoven" is applied to a wide range of products which in term of their properties are located between the groups of paper and cardboard on the one hand and textiles on the other hand. As regards nonwovens a large number of extremely varied production processes are used, such as airlaid, wetlaid, spunlaced, spunbond, meltblown techniques etc. The fibres may be in the form of endless fibres or fibres prefabricated with an endless length, as synthetic fibres produced in situ or in the form of staple fibres. Alternatively, they may be made from natural fibres or from blends of synthetic fibres and natural fibres.

By "absorbent article" is meant an article that absorbs or is adapted to absorb bodily fluids, such as urine and/or blood.

Although the description of the various variants, alternatives and example embodiments in conjunction with the figures above refers to the fastening component, and sometimes to the fastening component 11a, said description is applicable to all of the fastening components and the mating fastening components of the article unless explicitly stated above. Further, it should be readily appreciated that when a variant, an alternative or an example embodiment is described in relation to the fastening component 11a and mating fastening component 13a, said variant, alternative or example embodiment may likewise be applicable to the fastening component 11b and mating fastening component 13b of the article, unless explicitly stated above.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. An absorbent article, said article having a longitudinal direction, a transverse direction, an inner surface configured to face the user during use, an outer surface configured to face away from the user during use, wherein said article comprises, as seen in the longitudinal direction:

a first body portion, a second body portion and an intermediate crotch portion provided with two leg openings, the crotch portion extending between the first body portion and the second body portion in the longitudinal direction of the article, wherein outer longitudinal edge portions of the first body portion are adapted to be interconnected to outer longitudinal edge portions of the second body portion by first and second longitudinal refastenable side seam configurations, each one of the refastenable side seam configurations comprises a fastening component bonded to an outer longitudinal edge portion of the first body portion and a mating fastening component bonded to a corresponding outer longitudinal edge portion of the second body portion, wherein each one of the fastening components and the mating fastening components comprises a first mechanical connector structure and a second mechanical connector structure, each first mechanical connector structure being capable of forming a mechanical interconnection with said second mechanical connector structure, and being incapable of forming a mechanical interconnection with an identical structure, whereby corresponding fastening component and mating fastening component of each refastenable side seam configuration are mechanically connectable via said first mechanical connector structure and said second mechanical connector structure to form an interconnection so as to form a pant configuration, wherein any one of the fastening component and the mating fastening component displays a repeated pattern, each having a length and a width, wherein each one of the fastening components and mating fastening components having a length, and a longitudinal central axis being defined along said length, wherein said pattern formed by said first and said second connector structures is such that all portions of said first structure on one side of said longitudinal central axis mirrors a portion of said second structure on said other side of said longitudinal central axis, wherein a transversal central axis is defined along said width of each fastening component and mating fastening component, wherein said pattern formed by said first and second connector structures is such that all portions of said first structure on one side of said transversal central axis mirrors a portion of said second structure on the other side of said transversal central axis.

2. The article according to claim 1, wherein, for each refastenable side seam configuration, said first mechanical connector structure and the second mechanical connector structure of said fastening component is arranged in a first pattern and the first mechanical connector structure and the second mechanical connector structure of said mating fastening component is arranged in a second pattern, wherein said first pattern and said second pattern are formed so that at least a portion of the first mechanical connector structure of said fastening component mirrors at least a portion of the second mechanical connector structure of said mating fastening component and at least a portion of the second mechanical connector structure of said fastening component mirrors at least a portion of the first mechanical connector structure of said mating fastening component.

3. The article according to claim 2, wherein the entire first pattern is a mirror image of the entire second pattern.

4. The article according to claim 1, wherein the extension and orientation of the fastening component on the outer longitudinal edge portion of the first body portion, as seen in the direction x and direction y, corresponds to the extension and orientation of the mating fastening component on the outer longitudinal edge portion of the second body portion, as seen in the direction x and direction y.

5. The article according to claim 1, wherein one of said first and second mechanical connector structures comprises hooks, and the other of the first and the second mechanical connector structures comprises loops.

6. The article according to claim 1, wherein one of said first and second connector structures comprises a first type of hooks, and the other of the first and the second connector structures comprises a second type of hooks, said first type of hooks having different hook characteristics than said second type of hooks.

7. The article according to claim 1, wherein said first connector structure is provided by a first connector material and said second connector structure is provided by a second connector material.

8. The article according to claim 7, wherein said second connector material is attached to said first connector material.

9. The article according to claim 8, wherein any one of the fastening component and the mating fastening component comprises a first connector material onto which intermittent pieces of second connector material are attached.

10. The article according to claim 8, wherein any one of the fastening component and the mating fastening component comprises a first connector material onto which is attached a second connector material in which through holes are formed, such that the first connector structures of the first connector material is accessible via the through holes in the second connector material.

11. The article according to claim 7, wherein any one of the fastening component and the mating fastening component comprises a carrier material, onto which said first and/or second connector material is attached.

12. The article according to claim 1, wherein any one of the fastening component and the mating fastening component being a single connector material comprising a backing from which the mechanical connector structures extend.

13. The article according to claim 1, wherein any one of the fastening component and the mating fastening component displays a repeated pattern of first and second mechanical connector structures.

14. The article according to claim 1, wherein said length of the repeated pattern being a length with which the pattern repetition is evenly divisible.

15. The article in accordance with claim 1, wherein said at least one portion of said first structure, located on one side of said longitudinal central axis and on one side of said transversal central axis; mirrors a portion of said second structure on said other side of said longitudinal central axis and another portion of said second structure on said other side of said transversal central axis.

16. The article according to claim 1, wherein only one out of said first and second mechanical connector structures is located on one side of said longitudinal central axis.

17. The article according to claim 1, wherein the first body portion of the article comprises a pair of elastic front side panels to which the fastening components are bonded and/or the second body portions comprises a pair of elastic back side panels to which the mating fastening components are bonded.

18. The article according to claim 1, further comprising a topsheet, which may form the inner surface, an outer cover assembly forming the outer surface, and an absorbent core disposed between the topsheet and the outer cover assembly.

19. The article according to claim 1, wherein said first refastenable side seam configuration extends from the waist opening to the first leg opening and/or said second refastenable side seam configuration extends from the waist opening to the second leg opening.

* * * * *